(12) United States Patent
Altshuler et al.

(10) Patent No.: US 8,346,347 B2
(45) Date of Patent: Jan. 1, 2013

(54) SKIN OPTICAL CHARACTERIZATION DEVICE

(75) Inventors: Gregory Altshuler, Lincoln, MA (US); Guangming Wang, Bedford, MA (US); Henry Zenzie, Dover, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 826 days.

(21) Appl. No.: 11/522,124

(22) Filed: Sep. 15, 2006

(65) Prior Publication Data

US 2007/0060819 A1    Mar. 15, 2007

Related U.S. Application Data

(60) Provisional application No. 60/717,490, filed on Sep. 15, 2005.

(51) Int. Cl.
*A61B 6/00* (2006.01)
*G01J 1/42* (2006.01)
*A61B 18/18* (2006.01)
*A61B 5/06* (2006.01)

(52) U.S. Cl. ....................................................... 600/476
(58) Field of Classification Search ................. 250/252.1
See application file for complete search history.

(56) References Cited

U.S. PATENT DOCUMENTS

| | | | |
|---|---|---|---|
| 853,033 A | 5/1907 | Roberts | |
| 1,590,283 A | 6/1926 | Catlin | |
| 1,676,183 A | 7/1928 | Garfunkle | |
| 1,706,161 A | 3/1929 | Hollnagen | |
| 2,472,385 A | 6/1949 | Rollman | |
| 2,669,771 A | 2/1954 | Burge et al. | |
| 3,261,978 A | 7/1966 | Brenman | |
| 3,327,712 A | 6/1967 | Kaufmann | |
| 3,486,070 A | 12/1969 | Engel | |
| 3,527,932 A | 9/1970 | Thomas | |
| 3,538,919 A | 11/1970 | Meyer | |
| 3,597,652 A | 8/1971 | Gates, Jr. | |
| 3,622,743 A | 11/1971 | Muncheryan | |
| 3,653,778 A | 4/1972 | Freiling | |
| 3,667,454 A | 6/1972 | Prince | |
| 3,693,623 A | 9/1972 | Harte et al. | |
| 3,793,723 A | 2/1974 | Kuris et al. | |

(Continued)

FOREIGN PATENT DOCUMENTS

AT        400305        4/1995

(Continued)

OTHER PUBLICATIONS

US 6,230,044, 05/2001, Afanassieva et al. (withdrawn).

(Continued)

*Primary Examiner* — Long V. Le
*Assistant Examiner* — Angela M Hoffa
(74) *Attorney, Agent, or Firm* — Thomas J. Engellenner; Reza Mollaghababa; Pepper Hamilton LLP

(57) ABSTRACT

The present invention is generally directed to dermatological devices and methods in which one or more skin characteristics, such as the melanin index, are determined by analyzing radiation backscattered from a skin region illuminated by at least one, and preferably, two or more wavelengths, e.g., in a range of about 600 nm to about 900 nm. In many embodiments, the radiation is coupled to the skin via a waveguide, and an optical sensor is employed to ascertain contact between the waveguide (e.g., a waveguide surface adapted for contact with the skin) and the skin.

47 Claims, 17 Drawing Sheets

U.S. PATENT DOCUMENTS

| | | |
|---|---|---|
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,890,537 A | 6/1975 | Park et al. |
| 3,900,034 A | 8/1975 | Katz et al. |
| 3,909,649 A | 9/1975 | Arsena |
| 3,939,560 A | 2/1976 | Lyall |
| 3,977,083 A | 8/1976 | Leslie et al. |
| 4,047,106 A | 9/1977 | Robinson |
| 4,213,462 A | 7/1980 | Sato |
| 4,233,493 A | 11/1980 | Nath |
| 4,254,333 A * | 3/1981 | Bergstrom .................... 250/221 |
| 4,269,067 A | 5/1981 | Tynan et al. |
| 4,273,109 A | 6/1981 | Enderby |
| 4,275,335 A | 6/1981 | Ishida |
| 4,298,005 A | 11/1981 | Mutzhas |
| 4,316,467 A | 2/1982 | Muckerheide |
| 4,333,197 A | 6/1982 | Kuris |
| 4,335,726 A | 6/1982 | Kolstedt |
| 4,388,924 A | 6/1983 | Weissman et al. |
| 4,409,479 A | 10/1983 | Sprague et al. |
| 4,452,081 A | 6/1984 | Seppi |
| 4,456,872 A | 6/1984 | Froeschle |
| 4,461,294 A | 7/1984 | Baron |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle |
| 4,561,440 A | 12/1985 | Kubo et al. |
| 4,566,271 A | 1/1986 | French et al. |
| 4,591,762 A | 5/1986 | Nakamura |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,629,884 A * | 12/1986 | Bergstrom ............... 250/227.21 |
| 4,653,495 A | 3/1987 | Nanaumi |
| 4,677,347 A | 6/1987 | Nakamura |
| 4,686,986 A | 8/1987 | Fenyo et al. |
| 4,695,697 A | 9/1987 | Kosa |
| 4,710,677 A | 12/1987 | Halberstadt et al. |
| 4,718,416 A | 1/1988 | Nanaumi |
| 4,733,660 A | 3/1988 | Itzkan |
| 4,736,745 A | 4/1988 | Gluckman |
| 4,745,909 A | 5/1988 | Pelton et al. |
| 4,747,660 A | 5/1988 | Nishioka et al. |
| 4,749,913 A | 6/1988 | Stuermer et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,819,669 A | 4/1989 | Politzer |
| 4,826,431 A | 5/1989 | Fujimura et al. |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,852,549 A | 8/1989 | Mori |
| 4,860,172 A | 8/1989 | Schlager et al. |
| 4,860,744 A | 8/1989 | Johnson et al. |
| 4,862,903 A | 9/1989 | Campbell |
| 4,871,479 A | 10/1989 | Bachelard et al. |
| 4,884,560 A | 12/1989 | Kuracina |
| 4,898,438 A | 2/1990 | Mori |
| 4,905,690 A | 3/1990 | Ohshiro et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,932,954 A | 6/1990 | Wondrazek et al. |
| 4,945,239 A | 7/1990 | Wist et al. |
| 4,973,848 A | 11/1990 | Kolobanov et al. |
| 4,976,308 A | 12/1990 | Faghri |
| 4,979,180 A | 12/1990 | Muncheryan |
| 4,992,256 A | 2/1991 | Skaggs et al. |
| 5,000,752 A | 3/1991 | Hoskin et al. |
| 5,030,090 A | 7/1991 | Maeda et al. |
| 5,032,178 A | 7/1991 | Cornell |
| 5,046,494 A | 9/1991 | Searfoss et al. |
| 5,050,597 A | 9/1991 | Daikuzono |
| 5,057,104 A | 10/1991 | Chess |
| 5,059,192 A | 10/1991 | Zaias |
| 5,065,515 A | 11/1991 | Iderosa |
| 5,066,293 A | 11/1991 | Furumoto |
| 5,071,417 A | 12/1991 | Sinofsky |
| 5,108,388 A | 4/1992 | Trokel |
| 5,127,395 A | 7/1992 | Bontemps |
| 5,133,102 A | 7/1992 | Sakuma et al. |
| 5,137,530 A | 8/1992 | Sand |
| 5,140,984 A | 8/1992 | Dew et al. |
| 5,159,601 A | 10/1992 | Huber |
| 5,160,194 A | 11/1992 | Feldman |
| 5,171,564 A | 12/1992 | Nathoo et al. |
| 5,178,617 A | 1/1993 | Kuizenga et al. |
| 5,182,557 A | 1/1993 | Lang |
| 5,182,857 A | 2/1993 | Simon |
| 5,192,278 A | 3/1993 | Hayes et al. |
| 5,196,004 A | 3/1993 | Sinofsky |
| 5,207,671 A | 5/1993 | Franken et al. |
| 5,222,907 A | 6/1993 | Katabuchi et al. |
| 5,225,926 A | 7/1993 | Cuomo et al. |
| 5,226,907 A | 7/1993 | Tankovich |
| 5,267,399 A | 12/1993 | Johnston |
| 5,281,211 A | 1/1994 | Parel et al. |
| 5,282,797 A | 2/1994 | Chess |
| 5,287,372 A | 2/1994 | Ortiz |
| 5,287,380 A | 2/1994 | Hsia |
| 5,293,880 A | 3/1994 | Levitt |
| 5,300,097 A | 4/1994 | Lerner et al. |
| 5,303,585 A | 4/1994 | Lichte |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,336,217 A | 8/1994 | Buys et al. |
| 5,342,358 A | 8/1994 | Daikuzono et al. |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,353,020 A | 10/1994 | Schurmann |
| 5,353,790 A * | 10/1994 | Jacques et al. ................ 600/315 |
| 5,356,081 A | 10/1994 | Sellar |
| 5,358,503 A | 10/1994 | Bertwell et al. |
| 5,360,426 A | 11/1994 | Muller et al. |
| 5,369,831 A | 12/1994 | Bock |
| 5,380,317 A | 1/1995 | Everett et al. |
| 5,386,427 A | 1/1995 | Zayhowski |
| 5,403,306 A | 4/1995 | Edwards et al. |
| 5,405,368 A | 4/1995 | Eckhouse |
| 5,409,446 A | 4/1995 | Rattner |
| 5,415,654 A | 5/1995 | Daikuzono |
| 5,422,112 A | 6/1995 | Williams |
| 5,425,728 A | 6/1995 | Tankovich |
| 5,425,735 A | 6/1995 | Rosen et al. |
| 5,425,754 A | 6/1995 | Braun et al. |
| 5,445,608 A | 8/1995 | Chen et al. |
| 5,445,611 A | 8/1995 | Eppstein et al. |
| 5,454,807 A | 10/1995 | Lennox et al. |
| 5,458,140 A | 10/1995 | Eppstein et al. |
| 5,474,549 A | 12/1995 | Ortiz et al. |
| 5,486,170 A | 1/1996 | Winston et al. |
| 5,486,172 A | 1/1996 | Chess |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,527,368 A | 6/1996 | Supkis et al. |

| | | | | | | |
|---|---|---|---|---|---|---|
| 5,531,739 A | 7/1996 | Trelles | | 5,879,159 A | 3/1999 | Cipolla |
| 5,531,740 A | 7/1996 | Black | | 5,883,471 A | 3/1999 | Rodman et al. |
| 5,536,168 A | 7/1996 | Bourke et al. | | 5,885,211 A | 3/1999 | Eppstein et al. |
| 5,549,660 A | 8/1996 | Mendes et al. | | 5,885,273 A | 3/1999 | Eckhouse et al. |
| 5,558,667 A | 9/1996 | Yarborough et al. | | 5,885,274 A | 3/1999 | Fullmer et al. |
| 5,561,881 A | 10/1996 | Klinger et al. | | 5,891,063 A | 4/1999 | Vigil |
| 5,571,098 A | 11/1996 | Domankevitz et al. | | 5,893,828 A | 4/1999 | Uram |
| 5,578,866 A | 11/1996 | DePoorter et al. | | 5,895,350 A | 4/1999 | Hori |
| 5,595,568 A | 1/1997 | Anderson et al. | | 5,897,549 A | 4/1999 | Tankovich |
| 5,611,793 A | 3/1997 | Wilson et al. | | 5,906,609 A | 5/1999 | Assa et al. |
| 5,616,140 A | 4/1997 | Prescott | | 5,908,418 A | 6/1999 | Dority et al. |
| 5,618,284 A | 4/1997 | Sand | | 5,913,833 A | 6/1999 | Elstrom et al. |
| 5,620,478 A | 4/1997 | Eckhouse et al. | | 5,913,883 A | 6/1999 | Alexander et al. |
| 5,626,631 A | 5/1997 | Eckhouse et al. | | 5,916,211 A | 6/1999 | Quon et al. |
| 5,628,744 A | 5/1997 | Coleman et al. | | 5,920,374 A | 7/1999 | Vaphiades et al. |
| 5,630,811 A | 5/1997 | Miller | | 5,921,926 A | 7/1999 | Rolland et al. |
| 5,634,711 A | 6/1997 | Kennedy et al. | | 5,928,222 A | 7/1999 | Kleinerman |
| 5,649,972 A | 7/1997 | Hochstein | | 5,944,687 A | 8/1999 | Benett et al. |
| 5,652,481 A | 7/1997 | Johnson et al. | | 5,944,748 A | 8/1999 | Mager et al. |
| 5,653,706 A | 8/1997 | Zavislan et al. | | 5,948,011 A | 9/1999 | Knowlton |
| 5,655,547 A | 8/1997 | Karni | | 5,949,222 A | 9/1999 | Buono |
| 5,657,760 A | 8/1997 | Ying et al. | | 5,954,710 A | 9/1999 | Paolini et al. |
| 5,658,148 A | 8/1997 | Neuberger et al. | | 5,955,490 A | 9/1999 | Kennedy et al. |
| 5,658,323 A | 8/1997 | Miller | | 5,957,915 A | 9/1999 | Trost |
| 5,660,836 A | 8/1997 | Knowlton | | 5,964,749 A | 10/1999 | Eckhouse et al. |
| 5,661,744 A | 8/1997 | Murakami et al. | | 5,968,033 A | 10/1999 | Fuller et al. |
| 5,662,643 A | 9/1997 | Kung et al. | | 5,968,034 A | 10/1999 | Fullmer et al. |
| 5,662,644 A | 9/1997 | Swor | | 5,974,059 A | 10/1999 | Dawson |
| 5,673,451 A | 10/1997 | Moore et al. | | 5,974,616 A | 11/1999 | Dreyfus |
| 5,679,113 A | 10/1997 | Caisey et al. | | 5,977,723 A | 11/1999 | Yoon |
| 5,683,380 A | 11/1997 | Eckhouse et al. | | 5,979,454 A | 11/1999 | Anvari et al. |
| 5,692,509 A | 12/1997 | Voss et al. | | 5,984,915 A | 11/1999 | Loeb et al. |
| 5,698,866 A | 12/1997 | Doiron et al. | | 6,007,219 A | 12/1999 | O'Meara |
| 5,707,403 A | 1/1998 | Grove et al. | | 6,015,404 A | 1/2000 | Altshuler et al. |
| 5,707,409 A | 1/1998 | Martin et al. | | 6,022,316 A | 2/2000 | Eppstein et al. |
| 5,713,738 A | 2/1998 | Yarborough | | 6,026,828 A | 2/2000 | Altshuler |
| 5,714,119 A | 2/1998 | Kawagoe et al. | | 6,027,495 A | 2/2000 | Miller |
| 5,720,772 A | 2/1998 | Eckhouse | | 6,029,303 A | 2/2000 | Dewan |
| 5,722,397 A | 3/1998 | Eppstein | | 6,029,304 A | 2/2000 | Hulke et al. |
| 5,725,522 A | 3/1998 | Sinofsky | | 6,030,378 A | 2/2000 | Stewart |
| 5,728,090 A | 3/1998 | Martin et al. | | 6,030,399 A | 2/2000 | Ignotz et al. |
| 5,735,844 A | 4/1998 | Anderson et al. | | 6,032,071 A | 2/2000 | Binder |
| 5,735,884 A | 4/1998 | Thompson et al. | | RE36,634 E | 3/2000 | Ghaffari |
| 5,738,678 A | 4/1998 | Patel | | 6,036,684 A | 3/2000 | Tankovich et al. |
| 5,742,392 A | 4/1998 | Anderson et al. | | 6,044,514 A | 4/2000 | Kaneda et al. |
| 5,743,901 A | 4/1998 | Grove et al. | | 6,050,990 A | 4/2000 | Tankovich et al. |
| 5,743,902 A | 4/1998 | Trost | | D424,197 S | 5/2000 | Sydlowski et al. |
| 5,746,735 A | 5/1998 | Furumoto et al. | | 6,056,548 A | 5/2000 | Neuberger et al. |
| 5,748,822 A | 5/1998 | Miura et al. | | 6,056,738 A | 5/2000 | Marchitto et al. |
| 5,755,751 A | 5/1998 | Eckhouse | | 6,058,937 A | 5/2000 | Doiron et al. |
| 5,759,200 A | 6/1998 | Azar | | 6,059,820 A | 5/2000 | Baronov |
| 5,760,362 A | 6/1998 | Eloy | | 6,063,108 A | 5/2000 | Salansky et al. |
| 5,769,076 A | 6/1998 | Maekawa et al. | | 6,070,092 A | 5/2000 | Kazama et al. |
| 5,782,249 A | 7/1998 | Weber et al. | | 6,071,239 A | 6/2000 | Cribbs et al. |
| 5,802,136 A | 9/1998 | Carol | | 6,074,382 A | 6/2000 | Asah et al. |
| 5,810,801 A | 9/1998 | Anderson et al. | | 6,080,146 A | 6/2000 | Altshuler et al. |
| 5,812,567 A | 9/1998 | Jeon et al. | | 6,080,147 A | 6/2000 | Tobinick |
| 5,813,855 A | 9/1998 | Crisio, Jr. | | 6,083,217 A | 7/2000 | Tankovich |
| 5,814,008 A | 9/1998 | Chen et al. | | 6,086,363 A | 7/2000 | Moran et al. |
| 5,814,040 A | 9/1998 | Nelson et al. | | 6,086,580 A | 7/2000 | Mordon et al. |
| 5,814,041 A | 9/1998 | Anderson et al. | | 6,094,767 A | 8/2000 | Iimura |
| 5,817,089 A | 10/1998 | Tankovich et al. | | 6,096,029 A | 8/2000 | O'Donnell, Jr. |
| 5,820,625 A | 10/1998 | Izawa et al. | | 6,096,209 A | 8/2000 | O'Brien et al. |
| 5,820,626 A | 10/1998 | Baumgardner | | 6,099,521 A | 8/2000 | Shadduck |
| 5,824,023 A | 10/1998 | Anderson | | 6,104,959 A | 8/2000 | Spertell |
| 5,827,264 A | 10/1998 | Hohla | | 6,106,293 A | 8/2000 | Wiesel |
| 5,828,803 A | 10/1998 | Eckhouse | | 6,106,294 A | 8/2000 | Daniel |
| 5,830,208 A | 11/1998 | Muller | | 6,110,195 A | 8/2000 | Xie et al. |
| 5,835,648 A | 11/1998 | Narciso, Jr. et al. | | 6,113,559 A | 9/2000 | Klopotek |
| 5,836,877 A | 11/1998 | Zavislan | | 6,117,129 A | 9/2000 | Mukai |
| 5,836,999 A | 11/1998 | Eckhouse et al. | | 6,120,497 A | 9/2000 | Anderson et al. |
| 5,840,048 A | 11/1998 | Cheng | | 6,126,655 A | 10/2000 | Domankevitz et al. |
| 5,849,029 A | 12/1998 | Eckhouse et al. | | 6,129,723 A | 10/2000 | Anderson et al. |
| 5,851,181 A | 12/1998 | Talmor | | 6,135,774 A | 10/2000 | Hack et al. |
| 5,853,407 A | 12/1998 | Miller | | 6,142,650 A | 11/2000 | Brown et al. |
| 5,860,967 A | 1/1999 | Zavislan et al. | | 6,142,939 A | 11/2000 | Eppstein et al. |
| 5,868,731 A | 2/1999 | Budnik et al. | | 6,149,644 A | 11/2000 | Xie |
| 5,868,732 A | 2/1999 | Waldman et al. | | 6,149,895 A | 11/2000 | Kutsch |
| 5,871,480 A | 2/1999 | Tankovich | | 6,159,236 A | 12/2000 | Biel |

| | | |
|---|---|---|
| 6,162,055 A | 12/2000 | Montgomery et al. |
| 6,162,211 A | 12/2000 | Tankovich et al. |
| 6,162,212 A | 12/2000 | Kreindel et al. |
| 6,171,300 B1 | 1/2001 | Adams |
| 6,171,301 B1 | 1/2001 | Nelson et al. |
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,197,020 B1 | 3/2001 | O'Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,210,425 B1 | 4/2001 | Chen |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,075 B1 | 5/2001 | Furumoto |
| 6,229,831 B1 | 5/2001 | Nightingale et al. |
| 6,235,015 B1 | 5/2001 | Mead, III et al. |
| 6,235,016 B1 | 5/2001 | Stewart |
| 6,236,891 B1 | 5/2001 | Ingle et al. |
| 6,239,442 B1 | 5/2001 | Iimura et al. |
| 6,240,306 B1 | 5/2001 | Rohrscheib et al. |
| 6,245,093 B1 | 6/2001 | Li et al. |
| 6,251,127 B1 | 6/2001 | Biel |
| 6,254,388 B1 | 7/2001 | Yarborough |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,884 B1 * | 8/2001 | Altshuler et al. .................. 606/9 |
| 6,273,885 B1 | 8/2001 | Koop et al. |
| 6,280,438 B1 | 8/2001 | Eckhouse et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,713 B1 | 9/2001 | Russell |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,325,769 B1 | 12/2001 | Klopotek |
| 6,328,733 B1 | 12/2001 | Trost |
| 6,331,111 B1 | 12/2001 | Cao |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,350,261 B1 | 2/2002 | Domankevitz et al. |
| 6,350,276 B1 | 2/2002 | Knowlton |
| 6,354,370 B1 | 3/2002 | Miller et al. |
| 6,355,054 B1 | 3/2002 | Neuberger et al. |
| 6,358,242 B1 | 3/2002 | Cecchetti |
| 6,358,272 B1 | 3/2002 | Wilden |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,395,016 B1 | 5/2002 | Oron et al. |
| 6,400,011 B1 | 6/2002 | Miki |
| 6,402,739 B1 | 6/2002 | Neev |
| 6,406,474 B1 | 6/2002 | Neuberger et al. |
| 6,409,665 B1 | 6/2002 | Scott et al. |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,443,978 B1 | 9/2002 | Zharov et al. |
| 6,451,007 B1 | 9/2002 | Koop et al. |
| 6,461,296 B1 | 10/2002 | Desai |
| 6,464,694 B1 | 10/2002 | Massengill |
| 6,471,712 B2 | 10/2002 | Burres |
| 6,471,716 B1 | 10/2002 | Pecukonis |
| 6,475,211 B2 | 11/2002 | Chess et al. |
| 6,484,052 B1 | 11/2002 | Visuri et al. |
| 6,485,413 B1 | 11/2002 | Boppart et al. |
| 6,491,685 B2 | 12/2002 | Visuri et al. |
| 6,494,900 B1 | 12/2002 | Salansky et al. |
| 6,497,702 B1 | 12/2002 | Bernaz |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,530,915 B1 | 3/2003 | Eppstein et al. |
| 6,537,270 B1 | 3/2003 | Elbrecht et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger et al. |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,616,447 B1 | 9/2003 | Rizoiu et al. |
| 6,616,451 B1 | 9/2003 | Rizolu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,652,459 B2 | 11/2003 | Payne et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,675,425 B1 | 1/2004 | Iimura |
| 6,676,654 B1 | 1/2004 | Balle-Petersen et al. |
| 6,679,837 B2 | 1/2004 | Daikuzono |
| 6,685,639 B1 | 2/2004 | Wang et al. |
| 6,685,699 B1 | 2/2004 | Eppstein et al. |
| 6,689,124 B1 | 2/2004 | Thiberg |
| 6,692,456 B1 | 2/2004 | Eppstein et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,746,444 B2 | 6/2004 | Key |
| 6,749,623 B1 | 6/2004 | Hsi et al. |
| 6,770,069 B1 | 8/2004 | Hobart et al. |
| 6,790,205 B1 | 9/2004 | Yamazaki et al. |
| 6,801,595 B2 | 10/2004 | Grodzins et al. |

| | | | | | | |
|---|---|---|---|---|---|---|
| 6,808,331 B2 | 10/2004 | Hall et al. | | 2001/0024777 A1 | 9/2001 | Azar et al. |
| 6,808,532 B2 | 10/2004 | Andersen et al. | | 2001/0025173 A1 | 9/2001 | Ritchie et al. |
| RE38,670 E | 12/2004 | Asah et al. | | 2001/0041886 A1 | 11/2001 | Durkin et al. |
| 6,858,009 B2 | 2/2005 | Kawata et al. | | 2001/0046652 A1 | 11/2001 | Ostler et al. |
| 6,860,879 B2 | 3/2005 | Irion et al. | | 2001/0048077 A1* | 12/2001 | Afanassieva ............. 250/339.08 |
| 6,862,771 B1 | 3/2005 | Muller | | 2002/0004066 A1 | 1/2002 | Stanley et al. |
| 6,863,781 B2 | 3/2005 | Nocera et al. | | 2002/0005475 A1 | 1/2002 | Zenzie |
| 6,878,144 B2 | 4/2005 | Altshuler et al. | | 2002/0013572 A1 | 1/2002 | Berlin |
| 6,881,212 B1 | 4/2005 | Clement et al. | | 2002/0016587 A1 | 2/2002 | Furumoto |
| 6,887,260 B1 | 5/2005 | McDaniel | | 2002/0018754 A1 | 2/2002 | Sagel et al. |
| 6,888,319 B2 | 5/2005 | Inochkin et al. | | 2002/0019624 A1 | 2/2002 | Clement et al. |
| 6,893,259 B1 | 5/2005 | Reizenson | | 2002/0026225 A1 | 2/2002 | Segal |
| 6,902,397 B2 | 6/2005 | Farrell et al. | | 2002/0029071 A1 | 3/2002 | Whitehurst |
| 6,902,563 B2 | 6/2005 | Wilkens et al. | | 2002/0049483 A1 | 4/2002 | Knowlton |
| 6,936,046 B2 | 8/2005 | Hissong et al. | | 2002/0058890 A1 | 5/2002 | Visuri et al. |
| 6,942,658 B1 | 9/2005 | Rizoiu et al. | | 2002/0071287 A1 | 6/2002 | Haase |
| 6,953,341 B2 | 10/2005 | Black | | 2002/0071827 A1 | 6/2002 | Petersen et al. |
| 6,974,451 B2 | 12/2005 | Altshuler et al. | | 2002/0072676 A1* | 6/2002 | Afanassieva ................ 600/473 |
| 6,976,985 B2 | 12/2005 | Altshuler et al. | | 2002/0081555 A1 | 6/2002 | Wiesel |
| 6,989,023 B2 | 1/2006 | Black | | 2002/0090725 A1 | 7/2002 | Simpson et al. |
| 6,991,644 B2 | 1/2006 | Spooner et al. | | 2002/0091377 A1 | 7/2002 | Anderson et al. |
| 6,997,923 B2 | 2/2006 | Anderson et al. | | 2002/0108193 A1 | 8/2002 | Gruber |
| 7,001,413 B2 | 2/2006 | Butler | | 2002/0111610 A1 | 8/2002 | Nordquist |
| 7,006,223 B2 | 2/2006 | Mullani | | 2002/0120256 A1 | 8/2002 | Furuno et al. |
| 7,029,469 B2 | 4/2006 | Vasily | | 2002/0123745 A1 | 9/2002 | Svaasand et al. |
| 7,033,349 B2 | 4/2006 | Key | | 2002/0127224 A1 | 9/2002 | Chen |
| 7,041,100 B2 | 5/2006 | Kreindel | | 2002/0128635 A1 | 9/2002 | Altshuler et al. |
| 7,044,959 B2 | 5/2006 | Anderson et al. | | 2002/0128695 A1 | 9/2002 | Harth et al. |
| 7,060,061 B2 | 6/2006 | Altshuler et al. | | 2002/0161357 A1 | 10/2002 | Anderson et al. |
| 7,066,733 B2 | 6/2006 | Logan et al. | | 2002/0161418 A1 | 10/2002 | Wilkens et al. |
| 7,070,611 B2 | 7/2006 | Biel | | 2002/0173780 A1 | 11/2002 | Altshuler et al. |
| 7,077,840 B2 | 7/2006 | Altshuler et al. | | 2002/0182563 A1 | 12/2002 | Boutoussov et al. |
| 7,081,128 B2 | 7/2006 | Hart et al. | | 2002/0183808 A1 | 12/2002 | Biel |
| 7,097,639 B1 | 8/2006 | Almeida | | 2002/0198517 A1 | 12/2002 | Alfano et al. |
| 7,097,656 B1 | 8/2006 | Akopov et al. | | 2003/0004499 A1 | 1/2003 | McDaniel |
| 7,135,033 B2 | 11/2006 | Altshuler et al. | | 2003/0009158 A1 | 1/2003 | Perricone |
| 7,144,247 B2 | 12/2006 | Black | | 2003/0009205 A1 | 1/2003 | Biel |
| 7,144,248 B2 | 12/2006 | Irwin | | 2003/0018373 A1 | 1/2003 | Eckhardt et al. |
| 7,144,105 B2 | 12/2006 | Gaulard | | 2003/0023235 A1 | 1/2003 | Cense et al. |
| 7,145,108 B2 | 12/2006 | Kanel et al. | | 2003/0023283 A1 | 1/2003 | McDaniel |
| 7,160,289 B2 | 1/2007 | Cohen | | 2003/0023284 A1 | 1/2003 | Gartstein et al. |
| 7,182,760 B2 | 2/2007 | Kubota | | 2003/0028227 A1 | 2/2003 | Neuberger et al. |
| 7,198,634 B2 | 4/2007 | Harth et al. | | 2003/0032900 A1 | 2/2003 | Ella |
| 7,204,832 B2 | 4/2007 | Altshuler et al. | | 2003/0032950 A1 | 2/2003 | Altshuler et al. |
| 7,220,254 B2 | 5/2007 | Altshuler et al. | | 2003/0036680 A1 | 2/2003 | Black |
| 7,223,270 B2 | 5/2007 | Altshuler et al. | | 2003/0040739 A1 | 2/2003 | Koop |
| 7,223,281 B2 | 5/2007 | Altshuler et al. | | 2003/0055414 A1 | 3/2003 | Altshuler et al. |
| 7,255,691 B2 | 8/2007 | Tolkoff et al. | | 2003/0057875 A1 | 3/2003 | Inochkin et al. |
| 7,274,155 B2 | 9/2007 | Inochkin et al. | | 2003/0059738 A1 | 3/2003 | Neuberger |
| 7,276,058 B2 | 10/2007 | Altshuler et al. | | 2003/0065314 A1 | 4/2003 | Altshuler et al. |
| 7,291,140 B2 | 11/2007 | MacFarland et al. | | 2003/0083649 A1 | 5/2003 | Margaron et al. |
| 7,291,141 B2 | 11/2007 | Jay | | 2003/0084534 A1 | 5/2003 | Kaizuka |
| 7,309,335 B2 | 12/2007 | Altshuler et al. | | 2003/0097122 A1 | 5/2003 | Ganz et al. |
| 7,311,722 B2 | 12/2007 | Larsen | | 2003/0100936 A1 | 5/2003 | Altshuler et al. |
| 7,322,972 B2 | 1/2008 | Viator et al. | | 2003/0104340 A1 | 6/2003 | Clemans |
| 7,329,273 B2 | 2/2008 | Altshuler et al. | | 2003/0109787 A1 | 6/2003 | Black |
| 7,329,274 B2 | 2/2008 | Altshuler et al. | | 2003/0109860 A1 | 6/2003 | Black |
| 7,331,953 B2 | 2/2008 | Manstein et al. | | 2003/0113684 A1 | 6/2003 | Scott |
| 7,331,964 B2 | 2/2008 | Maricle et al. | | 2003/0129154 A1 | 7/2003 | McDaniel |
| 7,333,698 B2 | 2/2008 | Israel | | 2003/0130709 A1 | 7/2003 | D.C. et al. |
| 7,351,252 B2 | 4/2008 | Altshuler et al. | | 2003/0152528 A1 | 8/2003 | Singh et al. |
| 7,422,598 B2 | 9/2008 | Altshuler et al. | | 2003/0163884 A1 | 9/2003 | Weihrauch |
| 7,423,767 B2 | 9/2008 | Steinsiek et al. | | 2003/0167080 A1 | 9/2003 | Hart et al. |
| 7,431,419 B2 | 10/2008 | Turner et al. | | 2003/0169433 A1 | 9/2003 | Koele et al. |
| 7,531,967 B2 | 5/2009 | Inochkin et al. | | 2003/0181896 A1 | 9/2003 | Zvuloni et al. |
| 7,540,869 B2 | 6/2009 | Altshuler et al. | | 2003/0187486 A1 | 10/2003 | Savage et al. |
| 7,624,640 B2 | 12/2009 | Maris et al. | | 2003/0195494 A1 | 10/2003 | Altshuler et al. |
| 7,647,092 B2* | 1/2010 | Motz et al. ..................... 600/478 | | 2003/0199859 A1 | 10/2003 | Altshuler et al. |
| 7,758,621 B2 | 7/2010 | Altshuler et al. | | 2003/0216719 A1 | 11/2003 | Debenedictis et al. |
| 7,763,016 B2 | 7/2010 | Altshuler et al. | | 2003/0216795 A1 | 11/2003 | Harth et al. |
| 7,935,107 B2 | 5/2011 | Altshuler et al. | | 2003/0232303 A1 | 12/2003 | Black |
| 7,938,821 B2 | 5/2011 | Chan et al. | | 2004/0006332 A1 | 1/2004 | Black |
| 7,942,915 B2 | 5/2011 | Altshuler et al. | | 2004/0010298 A1 | 1/2004 | Altshuler et al. |
| 7,942,916 B2 | 5/2011 | Altshuler et al. | | 2004/0015156 A1 | 1/2004 | Vasily |
| 8,002,768 B1 | 8/2011 | Altshuler et al. | | 2004/0015158 A1 | 1/2004 | Chen et al. |
| 2001/0007068 A1 | 7/2001 | Ota et al. | | 2004/0019120 A1 | 1/2004 | Vargas et al. |
| 2001/0008973 A1 | 7/2001 | Van Zuylen et al. | | 2004/0019990 A1 | 2/2004 | Farrell et al. |
| 2001/0016732 A1 | 8/2001 | Hobart et al. | | 2004/0024388 A1 | 2/2004 | Altshuler |
| 2001/0023363 A1 | 9/2001 | Harth et al. | | 2004/0024430 A1 | 2/2004 | Bader et al. |

| | | |
|---|---|---|
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0111132 A1 | 6/2004 | Shenderova et al. |
| 2004/0116984 A1 | 6/2004 | Spooner et al. |
| 2004/0133251 A1 | 7/2004 | Altshuler et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162549 A1 | 8/2004 | Altshuler |
| 2004/0162596 A1 | 8/2004 | Altshuler et al. |
| 2004/0176754 A1 | 9/2004 | Island et al. |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2004/0204745 A1 | 10/2004 | Altshuler et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |
| 2005/0065531 A1 | 3/2005 | Cohen |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0143719 A1 | 6/2005 | Sink |
| 2005/0168158 A1 | 8/2005 | Inochkin et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0182389 A1 | 8/2005 | LaPorte et al. |
| 2005/0197681 A1 | 9/2005 | Barolet et al. |
| 2005/0215988 A1 | 9/2005 | Altshuler et al. |
| 2005/0220726 A1 | 10/2005 | Pauly et al. |
| 2005/0251118 A1 | 11/2005 | Anderson et al. |
| 2006/0004306 A1 | 1/2006 | Altshuler et al. |
| 2006/0004347 A1 | 1/2006 | Altshuler et al. |
| 2006/0009750 A1 | 1/2006 | Altshuler et al. |
| 2006/0020309 A1 | 1/2006 | Altshuler et al. |
| 2006/0047281 A1 | 3/2006 | Kreindel |
| 2006/0058712 A1 | 3/2006 | Altshuler et al. |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0100677 A1 | 5/2006 | Blumenkranz et al. |
| 2006/0122668 A1 | 6/2006 | Anderson et al. |
| 2006/0149343 A1 | 7/2006 | Altshulter et al. |
| 2006/0161143 A1 | 7/2006 | Altshuler et al. |
| 2006/0194164 A1 | 8/2006 | Altshuler et al. |
| 2006/0206103 A1 | 9/2006 | Altshuler et al. |
| 2006/0253176 A1 | 11/2006 | Caruso et al. |
| 2006/0271028 A1 | 11/2006 | Altshuler et al. |
| 2006/0287646 A1 | 12/2006 | Altshuler et al. |
| 2007/0027440 A1 | 2/2007 | Altshuler et al. |
| 2007/0038206 A1 | 2/2007 | Altshuler et al. |
| 2007/0049910 A1 | 3/2007 | Altshuler et al. |
| 2007/0060819 A1 | 3/2007 | Altshuler et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0121069 A1 | 5/2007 | Andersen et al. |
| 2007/0159592 A1 | 7/2007 | Rylander et al. |
| 2007/0185552 A1 | 8/2007 | Masotti et al. |
| 2007/0194717 A1 | 8/2007 | Belikov et al. |
| 2007/0198004 A1 | 8/2007 | Altshuler et al. |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0255355 A1 | 11/2007 | Altshuler et al. |
| 2007/0288071 A1 | 12/2007 | Rogers |
| 2008/0009842 A1 | 1/2008 | Manstein et al. |
| 2008/0058783 A1 | 3/2008 | Altshuler et al. |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0195183 A1 | 8/2008 | Botchkareva et al. |
| 2008/0214988 A1 | 9/2008 | Altshuler et al. |
| 2008/0294150 A1 | 11/2008 | Altshuler et al. |
| 2008/0294152 A1 | 11/2008 | Altshuler et al. |
| 2008/0306471 A1 | 12/2008 | Altshuler et al. |
| 2008/0319430 A1 | 12/2008 | Zenzie et al. |
| 2009/0048557 A1 | 2/2009 | Yeshurun et al. |
| 2009/0069741 A1 | 3/2009 | Altshuler et al. |
| 2009/0137995 A1 | 5/2009 | Altshuler et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2010/0036295 A1 | 2/2010 | Altshuler et al. |
| 2010/0145321 A1 | 6/2010 | Altshuler et al. |
| 2010/0204686 A1 | 8/2010 | Yaroslavksy et al. |
| 2010/0286673 A1 | 11/2010 | Altshuler et al. |
| 2010/0298744 A1 | 11/2010 | Altshuler et al. |
| 2011/0046523 A1 | 2/2011 | Altshuler et al. |
| 2011/0137230 A1 | 6/2011 | Altshuler et al. |
| 2011/0172651 A1 | 7/2011 | Altshuler et al. |
| 2011/0184334 A1 | 7/2011 | Altshuler et al. |
| 2011/0267830 A1 | 11/2011 | Altshuler et al. |

FOREIGN PATENT DOCUMENTS

| | | |
|---|---|---|
| AU | 1851583 A | 3/1984 |
| CN | 2053926 | 3/1990 |
| CN | 1073607 | 6/1993 |
| CN | 1182572 A | 5/1998 |
| CN | 1351483 A | 5/2002 |
| CN | 1535126 A | 10/2004 |
| DE | 3304230 A1 | 8/1984 |
| DE | 3719561 A1 | 1/1988 |
| DE | 3837248 A1 | 5/1990 |
| DE | 9102407 | 7/1991 |
| DE | 19803460 | 8/1999 |
| DE | 19944401 A1 | 3/2001 |
| DE | 10140715 A1 | 3/2002 |
| DE | 10112289 A1 | 9/2002 |
| DE | 10120787 | 1/2003 |
| EP | 0142671 A1 | 5/1985 |
| EP | 0172490 A1 | 2/1986 |
| EP | 0320080 A1 | 6/1989 |
| EP | 0324120 A1 | 7/1989 |
| EP | 0563953 | 10/1993 |
| EP | 0565331 A2 | 10/1993 |
| EP | 0593375 | 4/1994 |
| EP | 0598984 | 6/1994 |
| EP | 0709941 | 5/1996 |
| EP | 0724894 A2 | 8/1996 |
| EP | 0726083 A2 | 8/1996 |
| EP | 0736308 A2 | 10/1996 |
| EP | 0743029 A2 | 11/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |

| | | | | | | |
|---|---|---|---|---|---|---|
| EP | 0884066 | A2 | 12/1998 | WO | WO-9532441 | 11/1995 |
| EP | 0885629 | A2 | 12/1998 | WO | 96/22741 A1 | 8/1996 |
| EP | 0920840 | A2 | 6/1999 | WO | 96/24406 A1 | 8/1996 |
| EP | 0 927 544 | A2 | 7/1999 | WO | WO-9623447 | 8/1996 |
| EP | 0927544 | | 7/1999 | WO | WO-9625979 | 8/1996 |
| EP | 1038505 | A2 | 9/2000 | WO | WO-9628212 A1 | 9/1996 |
| EP | 1075854 | | 2/2001 | WO | WO-9636396 | 11/1996 |
| EP | 1138349 | A2 | 10/2001 | WO | WO-9641579 | 12/1996 |
| EP | 1147785 | A2 | 10/2001 | WO | WO-9713458 | 4/1997 |
| EP | 1219258 | A1 | 7/2002 | WO | WO-9713552 A1 | 4/1997 |
| EP | 1226787 | A2 | 7/2002 | WO | WO-9722384 | 6/1997 |
| EP | 1 238 683 | A1 | 9/2002 | WO | 97/28752 A1 | 8/1997 |
| EP | 1250893 | A2 | 10/2002 | WO | 98/07379 A1 | 2/1998 |
| EP | 1057454 | | 11/2003 | WO | WO-9804317 | 2/1998 |
| EP | 1457234 | | 9/2004 | WO | WO-9805286 A1 | 2/1998 |
| EP | 1495735 | A1 | 1/2005 | WO | WO-9805380 A1 | 2/1998 |
| EP | 1 512 373 | | 3/2005 | WO | WO-9806456 | 2/1998 |
| EP | 1512373 | A1 | 3/2005 | WO | 98/20937 A2 | 5/1998 |
| EP | 1 535 582 | | 6/2005 | WO | WO-9824507 | 6/1998 |
| EP | 1535582 | A1 | 6/2005 | WO | 98/29134 A2 | 7/1998 |
| EP | 1627662 | A1 | 2/2006 | WO | 98/41158 A1 | 9/1998 |
| EP | 1839705 | A1 | 10/2007 | WO | WO-9851235 | 11/1998 |
| EP | 1854505 | A2 | 11/2007 | WO | WO-9852481 | 11/1998 |
| FR | 2199453 | A1 | 4/1974 | WO | WO-9858595 | 12/1998 |
| FR | 2591902 | A1 | 6/1987 | WO | WO-9910046 | 3/1999 |
| GB | 1546625 | A | 5/1979 | WO | 99/17668 A1 | 4/1999 |
| GB | 2044908 | A | 10/1980 | WO | WO-9917666 | 4/1999 |
| GB | 2 059 053 | | 4/1981 | WO | WO-9917667 | 4/1999 |
| GB | 2 059 054 | | 4/1981 | WO | WO-9927997 | 6/1999 |
| GB | 2059053 | A | 4/1981 | WO | WO-9929243 | 6/1999 |
| GB | 2059054 | A | 4/1981 | WO | WO-9934867 A1 | 7/1999 |
| GB | 2123287 | A | 2/1984 | WO | WO-9938569 | 8/1999 |
| GB | 2239675 | A | 7/1991 | WO | WO-9943387 | 9/1999 |
| GB | 2270159 | A | 3/1994 | WO | WO-9944638 A1 | 9/1999 |
| GB | 2356570 | A | 5/2001 | WO | WO-9946005 | 9/1999 |
| GB | 2360461 | A | 9/2001 | WO | WO-9949937 | 10/1999 |
| GB | 2360946 | A | 10/2001 | WO | WO-9962472 | 12/1999 |
| GB | 2 364 376 | | 1/2002 | WO | WO-9966988 A1 | 12/1999 |
| GB | 2364376 | A | 1/2002 | WO | WO-0002491 | 1/2000 |
| GB | 2368020 | A | 4/2002 | WO | WO-0003257 A1 | 1/2000 |
| GB | 2390021 | A | 12/2003 | WO | WO-0007514 A1 | 2/2000 |
| GB | 2397528 | A | 7/2004 | WO | WO-0030741 A1 | 6/2000 |
| JP | 54-129791 | A | 10/1979 | WO | WO-0032272 | 6/2000 |
| JP | 64-027554 | A | 1/1989 | WO | WO-0040266 | 7/2000 |
| JP | 01-181877 | A | 7/1989 | WO | WO-0041278 A1 | 7/2000 |
| JP | 02-013014 | Y2 | 4/1990 | WO | WO-0043070 A1 | 7/2000 |
| JP | 2174804 | | 7/1990 | WO | WO-0044294 A1 | 8/2000 |
| JP | 3066387 | A | 3/1991 | WO | WO-0054649 A2 | 9/2000 |
| JP | 6022871 | | 2/1994 | WO | WO-0054685 A2 | 9/2000 |
| JP | 07-063957 | A | 3/1995 | WO | WO-0062700 A1 | 10/2000 |
| JP | 9084803 | A | 3/1997 | WO | 00/66226 A1 | 11/2000 |
| JP | 10014661 | | 1/1998 | WO | WO-0064537 | 11/2000 |
| JP | 10-503109 | A | 3/1998 | WO | WO-0071045 A1 | 11/2000 |
| JP | 10-099574 | A | 4/1998 | WO | WO-0074583 A1 | 12/2000 |
| JP | 10165410 | A | 6/1998 | WO | WO-0074781 A1 | 12/2000 |
| JP | 11047146 | A | 2/1999 | WO | WO-0078242 A1 | 12/2000 |
| JP | 2000037400 | A | 2/2000 | WO | WO-0103257 A1 | 1/2001 |
| JP | 2000-153003 | A | 6/2000 | WO | WO-0114012 A1 | 3/2001 |
| JP | 2000300684 | A | 10/2000 | WO | WO-0126573 A1 | 4/2001 |
| JP | 2001-029124 | A | 2/2001 | WO | WO-0134048 A1 | 5/2001 |
| JP | 2001145520 | A | 5/2001 | WO | WO-0154606 A1 | 8/2001 |
| JP | 2001-343560 | A | 12/2001 | WO | WO-0154770 | 8/2001 |
| JP | 2005-017796 | A | 1/2005 | WO | WO-0178830 A2 | 10/2001 |
| JP | 2005027702 | A | 2/2005 | WO | WO-0209813 A1 | 2/2002 |
| RU | 2082337 | C1 | 6/1997 | WO | WO-0226147 | 4/2002 |
| RU | 2089126 | C1 | 9/1997 | WO | WO-02053050 A1 | 7/2002 |
| RU | 2089127 | C1 | 9/1997 | WO | WO-02069825 A1 | 9/2002 |
| RU | 2096051 | C1 | 11/1997 | WO | WO-02078559 A1 | 10/2002 |
| RU | 2122848 | C1 | 12/1998 | WO | WO-02094116 A1 | 11/2002 |
| WO | WO-8602783 | | 5/1986 | WO | WO-03005883 A2 | 1/2003 |
| WO | WO-8804592 | A1 | 6/1988 | WO | WO-03049633 A1 | 6/2003 |
| WO | WO-9000420 | | 1/1990 | WO | WO-2004000150 | 12/2003 |
| WO | WO-9102562 | A1 | 3/1991 | WO | 2004/011848 A2 | 2/2004 |
| WO | WO-9113652 | A1 | 9/1991 | WO | WO-2004033040 A1 | 4/2004 |
| WO | WO-9216338 | | 10/1992 | WO | WO-2004037068 A2 | 5/2004 |
| WO | WO-9219165 | | 11/1992 | WO | WO-2004037287 A2 | 5/2004 |
| WO | WO-9305920 | | 4/1993 | WO | WO-2004073537 A2 | 9/2004 |
| WO | WO-9510243 | | 4/1995 | WO | WO-2004080279 A2 | 9/2004 |
| WO | WO-9515725 | | 6/1995 | WO | WO-2004084752 A2 | 10/2004 |

| | | | |
|---|---|---|---|
| WO | WO-2004086947 A2 | 10/2004 |
| WO | WO-2005007003 A1 | 1/2005 |
| WO | WO-2005009266 A1 | 2/2005 |
| WO | WO-2005030317 A2 | 4/2005 |
| WO | 2005/046793 A2 | 5/2005 |
| WO | WO-2005065288 A2 | 7/2005 |
| WO | WO-2005092438 A1 | 10/2005 |
| WO | WO-2005096981 A2 | 10/2005 |
| WO | WO-2005099369 A2 | 10/2005 |
| WO | WO-2005112815 A1 | 12/2005 |
| WO | WO-2006006123 A1 | 1/2006 |
| WO | WO-2006036968 A2 | 4/2006 |
| WO | 2006/066226 A1 | 6/2006 |
| WO | WO-2006089227 A2 | 8/2006 |
| WO | WO-2006101735 A1 | 9/2006 |
| WO | WO-2006116141 A1 | 11/2006 |
| WO | WO-2007035444 A2 | 3/2007 |
| WO | 2007/122611 A2 | 11/2007 |
| WO | WO-2008070747 A2 | 6/2008 |

OTHER PUBLICATIONS

Altea Therapeutics—Medicines Made Better (single page website print-out).

Altshuler et al., "Human Tooth as an Optical Device," SPIE vol. 1429 Holography and Interferometry and Optical Pattern Recognition in Biomedicine, pp. 95-104, 1991.

Altshuler et al., "Modern Optics and Dentistry," Laser in Dentistry, pp. 283-297, 1995.

Altshuler et al., "New Optical Effects in the Human Hard Tooth Tissues," Lasers and Medicine, Proc. SPIE vol. 1353, pp. 97-102, 1989.

Altshuler, G.B. et al., "Acoustic response of hard dental tissues to pulsed laser action," SPIE, vol. 2080, Dental Application of Lasers, pp. 97-103, 1993.

Altshuler, G.B. et al., "Extended theory of selective photothermolysis," Lasers in Surgery and Medicine, vol. 29, pp. 416-432, 2001.

Amy, R.L. et al., "Selective mitochondrial damage by a ruby laser microbeam: An electron microscopic study," Science, vol. 15, pp. 756-758, Nov. 1965.

Anderson, R.R. et al., "Selective photothermolysis: Precise microsurgery by selective absorption of pulsed radiation," Science, vol. 220, pp. 524-527, Apr. 1983.

Anderson, R.R. et al., "The optics of human skin," Journal of Investigative Dermatology, vol. 77, No. 1, pp. 13-19, 1981.

Apfelberg et al. "Analysis of Complications of Argon Laser Treatment for Port Wine Hemangiomas with Reference to Striped Technique," Lasers in Surgery and Medicine, 2:357-371 (1983).

Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).

Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.

"BIOPTRON Light Therapy System," website print-out, accessed Jul. 13, 2006 (2 pages).

Bjerring, P. et al., "Selective Non-Ablative Wrinkle Reduction by Laser," J Cutan Laser Ther, vol. 2, pp. 9-15, 2000.

Blankenau et al., "In Vivo Caries-Like Lesion Prevention with Argon Laser: Pilot Study," Journal of Clinical Laser Medicine and Surgery, vol. 17, No. 6, pp. 241-243, 1999.

Chan, E.K., "Effects of Compression on Soft Tissue Optical Properties," IEEE Journal of Selected Topics in Quantum Electronics, vol. 2, No. 4, pp. 943-950 (Dec. 1996).

Dabrowska, "Intravital Treatment of the Pulp with Stimulation Laser Biostimulation," Abstract Rocz-Akad-Med-Bialymst. 1997; 42(1): 168-76.

Derma Chiller advertisement (2 pages) from Paradigm Trex.

Dixon et al. "Hypertrophic Scarring in Argon Laser Treatment of Port-Wine Stains," Plastic and Reconstructive Surgery, 73:771-777 (1984).

Doukas et al., "Transdermal Drug Delivery With a Pressure Wave," Advanced Drug Delivery Reviews 56 (2004), pp. 559-579.

Dover, J.S. et al., "Pigmented guinea pig skin irradiated with Q-switched ruby laser pulses," Arch Dermatol, vol. 125, pp. 43-49, Jan. 1989.

Finkelstein, L.H. et al., "Epilation of hair-bearing urethral grafts using the neodymium:yag surgical laser," Journal of Urology, vol. 146, pp. 840-842, Sep. 1991.

Fiskerstrand, E.J. et al., "Hair Removal with Long Pulsed Diode Lasers: A Comparison Between Two Systems with Different Pulse Structures," Lasers in Surgery and Medicine, vol. 32, pp. 399-404, 2003.

Forrest-Winchester et al., "The Effect of Infrared Laser Radiation on Dentinal Permeability in vitro," Department of Dentistry, University of Queensland Dental School, pp. 1-8, 1992.

Ginsbach et al. "New Aspects in the Management of Benign Cutaneous Tumors," Laser 79 Opto-Electronics, Munich Conference Proceedings, 344-347 (1979).

Goldman, L. et al. "Treatment of basal cell epithelioma by laser radiation," JAMA, vol. 189, No. 10, pp. 773-775.

Goldman, L. et al., "Effect of the laser beam on the skin, III. Exposure of cytological preparations," Journal of Investigative Dermatology, vol. 42, pp. 247-251, 1964.

Goldman, L. et al., "Effect of the laser beam on the skin, Preliminary report" Journal of Investigative Dermatology, vol. 40, pp. 121-122, 1963.

Goldman, L. et al., "Impact of the laser on nevi and melanomas," Archives of Dermatology, vol. 90, pp. 71-75, Jul. 1964.

Goldman, L. et al., "Laser action at the cellular level," JAMA, vol. 198, No. 6, pp. 641-644, Nov. 1966.

Goldman, L. et al., "Laser treatment of tattoos, A preliminary survey of three year's clinical experience," JAMA, vol. 201, No. 11, pp. 841-844, Sep. 1967.

Goldman, L. et al., "Long-term laser exposure of a senile freckle," ArchEnviron Health, vol. 22, pp. 401-403, Mar. 1971.

Goldman, L. et al., "Pathology, Pathology of the effect of the laser beam on the skin," Nature, vol. 197, No. 4870, pp. 912-914, Mar. 1963.

Goldman, L. et al., "Preliminary investigation of fat embolization from pulsed ruby laser impacts of bone," Nature, vol. 221, pp. 361-363, Jan. 1969.

Goldman, L. et al., "Radiation from a Q-switched ruby laser, Effet of repeated impacts of power output of 10 megawatts on a tattoo of man," Journal of Investigative Dermatology, vol. 44, pp. 69-71, 1965.

Goldman, L. et al., "Replica microscopy and scanning electron microscopy of laser impacts on the skin," Journal of Investigative Dermatology, vol. 52, No. 1, pp. 18-24, 1969.

Goldman, L. et al., "The biomedical aspects of lasers," JAMA, vol. 188, No. 3, pp. 302-306, Apr. 1964.

Goldman, L. et al., "The effect of repeated exposures to laser beams," Acta derm.-vernereol., vol. 44, pp. 264-268, 1964.

Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

Goldman, L., "Effects of new laser systems on the skin," Arch Dermatol., vol. 108, pp. 385-390, Sep. 1973.

Goldman, L., "Laser surgery for skin cancer," New York State Journal of Medicine, pp. 1897-1900, Oct. 1977.

Goldman, L., "Surgery by laser for malignant melanoma," J. Dermatol. Surg. Oncol., vol. 5, No. 2, pp. 141-144, Feb. 1979.

Goldman, L., "The skin," Arch Environ Health, vol. 18, pp. 434-436, Mar. 1969.

Goldman, L., Biomedical Aspects of the Laser, Springer-Verlag New York Inc., publishers, Chapts. 1, 2 & 23, 1967.

Gottlieb, I., "Power Supplies, Switching Regulators, Inverters & Converters," 1976.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).

Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.

Grossman, M.C. et al., "Damage to hair follicles by normal-mode ruby laser pulses," Journal of he American Academy of Dermatology, vol. 35, No. 6, pp. 889-894, Dec. 1996.

Grossman, M.C. et al., "Laser Targeted at Hair Follicles," Lasers Med Surg., Suppl. 7:221 (1995).

Hicks et al., "After Low Fluence Argon Laser and Flouride Treatment," Compendium, vol. 18, No. 6, Jun. 1997.

Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998.

Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).

Hulsbergen Henning et al., "Port Wine Stain Coagulation Experiments with a 540-nm Continuous Wave Dye-Laser," Lasers in Surgery and Medicine, 2:205-210 (1983).

Invention description to certificate of authorship, No. 719439, "The ring resonator of optical quantum generator".

Invention description to certificate of authorship, No. 741747, "The modulator of optical radiation intensity".

Invention description to certificate of authorship, No. SU 1257475 A1, "Laser interferometric device to determine no-linearity of an index of refraction of optical medium".

Invention description to certificate of authorship, No. SU 1326962 A1, "The way of determination of non-linearity of an index of refraction of optical medium".

Invention description to certificate of autorship, No. 532304, "The way of investigation of radiation time structure of optical quantum generator".

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).

Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.

Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.

Karu, "Photobiological Fundamentals of Low-Power Laser Therapy," 8th Congress of International Society for Laser Surgery and Medicine, Mar. 30, 1987.

Kazmina et al., "Laser Prophlaxis and Treatment of Primary caries," SPIE vol. 1984, pp. 231-233.

Klein, E. et al., "Biological effects of laser radiation 1.,"Northeast Electroncis Research and Engineering Meeting, NEREM Record, IEEE catalogue No. F-60, pp. 108-109, 1965.

Kozlov et al., "Laser in Diagnostics and Treatment of Microcirculation Disorders Under Parodontitis," SPIE vol. 1984, pp. 253-264.

Kuhns, J.G. et al., "Biological effects of laser radiation II Effects of laser irradiation on the skin," NEREM Record, pp. 152-153, 1965.

Kuhns, J.G. et al., "Laser injury in skin," Laboratory Investigation, vol. 17, No. 1, pp. 1-13, Jul. 1967.

Levin, G. et al., "Designing with hyseretic current-mode control, " EDN Magazine, pp. 1-8, Apr. 11, 2006.

Levin, G. et al., "Designing with hyseretic current-mode control, " EDN Magazine, pp. 1-8, Apr. 28, 2004.

Maegawa, et al., "Effects of Near-Infrared Low-Level Laser Irradiation on Microcirculation," Lasers in Surgery and Medicine, vol. 27, pp. 427-437, 2000.

Mamedova et al., "Microbiological Estimate of Parodontis Laser Therapy Efficiency," SPIE vol. 1984, pp. 247-249.

Mang, "Effect of Soft Laser Treatment on Wound Healing in the Hamster Oral Mucosa," American Society for Laser Medicine and Surgery Abstracts, Chapters 25, pp. 5-8.

Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.

Margolis, R.J. et al., "Visible action spectrum for melanin-specific selective photothermolysis," Lasers in Surgery and Medicine, vol. 9, pp. 389-397, 1989.

Marinelli et al., "Diode laser illuminated automotive lamp systems," SPIE Proceedings vol. 3285:170-177 (1998).

McDaniel, et al., "Hexascan: A New Robotized Scanning Laser Handpiece," Cutis, 45:300-305 (1990).

Nemeth, et al., "Copper vapor laser treatment of pigmented lesions," Lasers Surg. Med. Supp. 2:51 (1990).

Ohbayashi, "Stimulatory Effect of Laser Irradiation on Calcified Nodule Formation in Human Dental Pulp Fibroblasts," Abstract J-Endod. Jan. 1999; 25(1): 30-3.

Ohshiro et al., "The Ruby and Argon Lasers in the Treatment of the Naevi," Annals Academy of Medicine, Apr. 1983, vol. 12, No. 2, pp. 388-395.

Oleinik, et al., "Automatized Securing Definition for Laser Therapy Indications in Case of Non-complicated Caries," SPIE, vol. 1984, pp. 238-244.

Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.

Osigo et al, "Phase Transitions of Rat Stratum Corneum Lipids by an Electron Paramagnetic Resonance Study and Relationship of Phase States to Drug Penetration," Biochimica et Biophysica Acta 1301:97-104 (1996).

Ozawa et al., "Stimulatory Effects of Low-Power Laser Irradiation on Bone Formation in vitro," SPIE vol. 1984, pp. 281-288.

Parrish, J.A., "Selective thermal effects with pulsed irradiation from lasers: From organ to organelle," Journal of Investigative Dermatology, vol. 80, No. 6 Supplement, pp. 75s-80s, 1983.

Petrischev et al. "Clinical and Experimental Low-Intense Laser Therapy in Dentistry," SPIE, vol. 1984, pp. 212-214.

Petrischev et al., "Report on Low Intensity Laser Radiation Usage in Dentistry," SPIE vol. 1984, pp. 202-211.

Polla, L. et al., "Melanosomes are a primary target of Q-switched ruby laser irradiation in guinea pig skin," Journal of Investigative Dermatology, vol. 89, No. 3, pp. 281-286, Sep. 1987.

Powell, "Laser Dental Decay Prevention: does it have a future?" SPIE vol. 3192, 1997.

Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).

Remillard et al., "Diode Laser Illuminators for Night-Vision Applications," SPIE Proceedings vol. 4285:14-22 (2001).

Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).

Rohrer, "Evaluating the Safety and Efficacy of a Novel Light Based Hair Removal System," Lasers. Surg. Med. Supp.13:97 (2001).

Rotteleur, et al., "Robotized scanning laser handpiece for the treatment of port wine stains and other angiodysplasias," Lasers Surg. Med., 8:283-287 (1998).

Rubach et al., "Histological and Clinical Evaluation of Facial Resurfacing Using a Carbon Dioxide Laser With the Computer Pattern Generator," Arch Otolaryngol Head Neck Surg., 123:929-934 (1997).

Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).

Sandford et al., "Thermal Effects During Desensitisation of Teeth with Gallium-Aluminum-Arsenide Lasers," University of Queensland Dental School, Periodontology 15:25-30 (1994).

Schindl, "Does Low Intensity Laser Irradiation Really Cause Cell Damage?" Laser in Surgery and Medicine vol. 22, pp. 105, 2001.

Sheehan-Dare, et al., "Lasers in Dermatology," British Journal of Dermatology, 129:1-8 (1993).

Shimbashi, T. et al., "Ruby laser treatment of pigmented skin lesions," Aesth. Plast. Surg., vol. 19, pp. 225-229, 1995.

Shimizu et al., "Prospect of Relieving Pain Due to Tooth Movement During Orthodontic Treatment Utilizing a GA-AI As Diode Laser," SPIE vol. 1984, pp. 275-280.

Shumilovitch et al., "Influence of Low Intensity Laser Radiation Upon the Microflora of Carious Cavities and Root Canal," SPIE vol. 1984, pp. 215-220.

Sing, "Electroacupuncture and Laser Stimulation Treatment: Evaluation by Somatosensory Evoked Potential in Conscious Rabbits," Abstract Am-J-Chin-Med. 1997; 25(3-4): 263-71.

Sliney et al., "Safety with Lasers and Other Optical Sources: A Comprehensive Handbook," Plenum Press, pp. 477-480 (1980).

Sokolova et al., "Low-intense Laser Radiation in Complex Treatment of Inflammatory Diseases of Parodontium," SPIE vol. 1984, pp. 234-237.

Stratton, K. et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

Sumian, C.C. et al., "A Preliminary Clinical and Histopathological Study of Laser Skin Resurfacing Using a frequency-Doubled Nd:YAG Laser After Application of Chromofilm®," Journal of Cutaneous Laser Therapy, vol. 1, pp. 159-166, 1999.

Sumian, C.C. et al., "Laser Skin Resurfacing Using a Frequency Doubled Nd:YAG Laser After Topical Application of an Exogenous Chromophore," Lasers in Surgery and Medicine, vol. 25, pp. 43-50, 1999.

Taylor, C.R. et al., "Treatment of tattoos by Q-switched ruby laser," Arch. Dermatol. vol. 126, pp. 893-899, Jul. 1990.

Tuchin, V.V., "Laser light scattering in biomedical diagnostics and therapy," Journal of Laser Applications, vol. 5, No. 2-3, pp. 43-60, 1993.

Unger, "Laser Hair Transplantation III, Computer-assisted Laser Transplanting," Dermatol. Surg., 21:1047-1055 (1995).

Van Bruegel, "Power Density and Exposure Time of He-Ne Irradiation Are More Important Than Total Energy Dose in Photo-Biomodulation of Human Fibroblasts in Vitro," Lasers in Surgery and Medicine, vol. 12 pp. 528-537, 1992.

Walsh, "Laser "Curettage": a Critical Analysis," Periodontology 14:4-12, 1993.

Walsh, "The Current Status of Low Level Laser Therapy in Dentistry. Part 1. Soft Tissue Applications" paper prepared by LJ Walsh, Department of Dentistry University of Queensland, pp. 1-16. Publication date unknown.

Watanabe, S. et al., "Comparative studies of femtosecond to microsecond laser pulses on selective pigmented cell injury in skin," Photochemistry and Photobiology, vol. 53, No. 6, pp. 757-762, 1991.

Watanabe, S. et al., "The Effect of Pulse Duration on Selective Pigmented Cell Injury by Dye Lasers," The Journal of Investigative Dermatology, 88:523, 1987.

Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.

Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.

Yules, R.B. et al., "The effect of Q-switched ruby laser radiation on dermal tattoo pigment in man," Arch Surg, vol. 95, pp. 179-180, Aug. 1967.

Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.

Zonios et al., "Skin Melanin, Hemoglobin, and Light Scattering Properties can be Quantitatively Assessed in Vivo Using Diffuse Reflectance Spectroscopy," Journal of Investigative Dermatology,117:1452-1457 (Dec. 2001).

International Preliminary Report on Patentability dated Oct. 8, 2007 corresponding to international application No. PCT/US2006/035927.

[No Author] IPG Data Sheet for TFL Thulium Laser, Jun. 2001.

[No Author] Webpage www.gallery.com—RUTILE (Titanium Oxide)—Retrieved Oct. 3, 2011 from Http://www.galleries.com/minerals/oxides/rutile/rutile.htm. 2 pages.

International Preliminary Report on Patentability mailed Oct. 8, 2007 for Applciation No. PCT/US2006/035927 (7 Pages).

* cited by examiner

LED 1 AND 2

RAW PIGMENTOMETER SIGNAL

ROCKING SENSITIVITY (660 vs 910 nm)

AIR GAP SENSITIVITY (660 vs 910 nm)

TIR COUPLING AND TIR DECOUPLING DESIGN

SKIN OPTICAL CHARACTERIZATION DEVICE

CROSS REFERENCE TO RELATED APPLICATIONS

This application claims priority to U.S. Provisional Patent Application Ser. No. 60/717,490 filed on Sep. 15, 2005, which is herein incorporated by reference in its entirety.

BACKGROUND

The present invention relates generally to diagnostic and therapeutic dermatological devices and methods that measure physical characteristics of tissue, such as, the skin.

Dermatological devices are used to improve a variety of skin conditions, such as removal of unwanted hair, skin rejuvenation, removal of vascular lesions, acne treatment, treatment of cellulite, pigmented lesions and psoriasis, tattoo removal, treatment of skin and other cancers, etc. Many of these devices typically target a chromophore in the tissue of the subject under treatment. Depending on the procedure, such a chromophore may be, for example, melanin, hemoglobin, lipid, water, or pigment of a tattoo.

Optimal use of these devices depends, at least in part, on accurate identification of the subject's skin pigmentation so that proper treatment parameters can be used. However, commonly used methods of skin typing are not generally based on actual measurements of the chromophores of interest, such as the amount of melanin in the skin. For example, the commonly used Fitzpatrick skin type scale, which ranges from very fair (skin type I) to very dark (skin type VI), is based solely on a person's complexion and response to sun exposure. In addition, such conventional skin typing methods do not take into account variations in the concentration of a chromophore in different parts of an individual's skin. For example, although different parts of an individual's skin can exhibit different melanin concentrations, the Fitzpatrick scale provides only a single skin type for that individual. As such, the use of such conventional skin typing methods may result in complications during treatment, such as burns, scars, or ineffective treatment.

Therefore, a need exists for dermatological and other devices and methods that can accurately and efficiently determine physical characteristics of a person's skin, such as, for example, skin melanin optical density (MOD), blood content, collagen content, and/or hydration. In addition, improved safety mechanisms are needed for dermatological devices so that they can be used for non-professional uses, such as home use.

SUMMARY OF THE INVENTION

In one aspect, the present invention provides a dermatological device for determining a physical characteristic of a portion of tissue that comprises a radiation source assembly configured to generate radiation having at least a first wavelength and a waveguide coupled to that source assembly for directing the radiation from the source to the tissue portion, where the waveguide has a surface configured to irradiate the tissue portion with the radiation. The device further includes a detector coupled to the waveguide and configured to detect radiation from the source, where the detector generates signals indicative of the level of radiation detected. A processor in communication with the detector processes the signals and calculates a physical characteristic of the tissue region. The detector can be configured to detect the radiation from the source after the portion of the tissue has been irradiated with the radiation from the source.

In a related aspect, the skin characteristic can be, e.g., any of melanin index, collagen contant, diffusion or erythema measurement.

In another aspect, the radiation source assembly can include two or more radiation sources. For example, the first radiation source can produce radiation having a first wavelength (or first wavelength band) and a second radiation source can produce radiation having a second wavelength (or second wavelength band). Alternatively, the radiation source assembly can include a single radiation source. The radiation source can produce radiation of more than one wavelength (i.e., radiation of a first wavelength and also radiation of a second wavelength), or radiation source assembly can be configured to generate radiation having two or more, or three or more wavelengths. The first and/or second wavelength can be selected from a range of about 350 nm to about 1200 nm, or from a range of about 600 nm to about 900 nm. In some embodiments, the radiation source assembly can include at least one of a light emitting diode (LED), a bi-color LED, a tunable radiation source, and/or a laser radiation source. The term "wavelength" as used herein is not necessarily limited to monochromatic light but rather can also define a line or band of wavelengths, depending upon the nature of the light source.

In another aspect, the device can further comprise a contact sensor indicating whether the surface of the optical waveguide is in contact with the skin. By way of example, the contact sensor can be configured to detect a level of the radiation at a wavelength generated by the source. In some embodiments wherein the radiation source assembly is configured to generate radiation having two or more wavelengths, the contact sensor can be configured to detect a level of the radiation at two or more of those wavelengths.

In a related aspect, in the above device, the contact sensor can be configured to send a signal to the processor indicating that the surface of the waveguide is not in contact with the tissue. For example, the contact sensor can send a signal when the contact sensor detects that the detected radiation level is below or above a threshold. The contact sensor can be optically coupled to the waveguide along a boundary, wherein the waveguide is configured to totally internally reflect the radiation along that boundary when the surface is not in contact with the tissue. Alternatively, the contact sensor can be optically coupled to the waveguide along a boundary, wherein the waveguide is configured to not totally internally reflect the radiation along that boundary when the surface is not in contact with the tissue.

In another aspect, the contact sensor can be configured to send a signal to the processor indicating that the surface of the waveguide is in contact with the tissue. For example, the contact sensor can detect that the detected radiation level is above or below a threshold. The contact sensor can be optically coupled to the waveguide along a boundary, wherein the waveguide is configured to not totally internally reflect the radiation along that boundary when the surface is in contact with the tissue. Alternatively, the contact sensor can be optically coupled to the waveguide along a boundary, wherein the waveguide is configured to totally internally reflect the radiation along that boundary when the surface is in contact with the tissue.

In another aspect, the device can further comprise two polarizers, one of which can be configured to filter radiation of a first polarity from the radiation source assembly and the other can be configured to filter radiation of a second polarity entering the contact sensor and/or entering the detector. The device can include a filter disposed between the contact sensor and the waveguide and/or between the waveguide and the detector.

In another aspect, the device can further comprise a controller coupled to the radiation source assembly. The controller can be configured to activate the radiation source assembly to produce radiation of different wavelengths at different times.

In another aspect, the waveguide can be formed of a material having an index of refraction in a range of about 1.4 to about 2.5. In some embodiments, the waveguide is an optical fiber. The device can further include at least one additional waveguide coupled to the source assembly. In some cases, that additional waveguide can be an optical fiber.

In another aspect, the invention discloses a dermatological device for determining a physical characteristic of a portion of tissue that comprises a radiation source assembly configured to generate radiation having first and second wavelengths, and a waveguide coupled to the source assembly for directing the radiation from the source to a portion of the tissue, and having a surface configured to irradiate that tissue portion with the radiation. The waveguide surface can be adapted for contact with the tissue and can inhibit transmission of radiation in absence of skin contact by total internal reflection of radiation reflected by a sidewall thereto. The device can further include a detector coupled to the waveguide and configured to detect radiation from the source, wherein the detector can generate signals indicative of the level of radiation detected. The detector can be configured to detect the radiation from the source after the portion of the tissue has been irradiated with the radiation from the source. A processor in communication with the detector can process the signals and calculate a physical characteristic of the tissue portion (e.g., a skin portion). In other words, the processor can determine a tissue (e.g., skin) characteristic based on the detector output.

In a related aspect, in the above device, a contact sensor optically coupled to the waveguide along a boundary can be configured to detect a level of the radiation transmitted through that boundary to determine whether said waveguide surface is in contact with the tissue.

In a related aspect, the first and second wavelengths can be in a range of about 300 nm to about 1200 nm, about 600 nm to about 900 nm, or about 630 nm to about 730 nm. For example, the first wavelength can be approximately 645 nm, or approximately 700 nm. In some embodiments, the first wavelength is approximately 645 nm and the second wavelength is approximately 700 nm.

In another related aspect, the device can further comprise a feedback mechanism in communication with the sensor and the source, wherein the feedback mechanism is capable of inhibiting activation of the source when the sensor indicates lack of optical contact between the waveguide and the source, and is capable of activating the source when the sensor indicates optical contact.

In another aspect, the invention provides a dermatological device with at least one radiation source, a waveguide optically coupled to the radiation source to transmit radiation from the source to the skin, the waveguide having two opposed surfaces and a sidewall extending between the surfaces. The device can further include a detector coupled to the waveguide to detect at least a portion of radiation backscattered from a skin region illuminated by the source radiation, and an optical contact sensor optically coupled to the sidewall, the sensor determining whether the waveguide is in contact with the skin based on detection of backscattered radiation leaking through the sidewall.

In yet another aspect, a dermatological device is disclosed comprising a radiation source assembly, a first waveguide having a proximal end adapted to receive radiation from the radiation source assembly and a distal end adapted to transmit radiation to a tissue, a second waveguide having a distal end adapted to receive backscattered radiation from the first waveguide and a proximal end adapted to transmit the backscattered radiation. The device can further include a detector optically coupled to the second waveguide and configured to measure a physical characteristic of the tissue; and a processor electrically coupled to the detector and configured to receive a signal from the detector corresponding to the backscattered radiation. The processor is configured to determine a physical characteristic of the tissue based on the backscattered radiation that is detected. The device can further include a means for coupling the backscattered radiation exiting from the proximal end to the detector, such as a beamsplitter. The radiation source assembly is capable of generating radiation at two or more wavelengths in a range of about 350 nm to about 1200 nm, or about 600 nm to about 900 nm. The device can further comprise additional waveguides, such as optical fibers.

In another aspect, the invention provides a dermatological device that comprises at least one source of radiation, an optical fiber receiving radiation from the source at a proximal end and applying the radiation to a skin region at a distal end, another optical fiber coupled at a distal end to skin at another region separated from the illuminated region by a skin segment so as to receive at least a portion of the applied radiation after transmission through that segment, a detector optically coupled to a proximal end of the another optical fiber to detect at least a portion of the transmitted radiation received by that fiber, the detector generating a signal indicative of an intensity of the received radiation, and a processor operating on the detector signal to determine a skin characteristic.

In another aspect, a method of determining a characteristic of tissue is disclosed that comprises the steps of applying radiation of first and second wavelengths from a waveguide to the tissue; detecting at least a portion of radiation of the first and second wavelengths backscattered from the tissue; generating at least one signal indicative of an intensity of the backscattered radiation, and processing the at least one signal to calculate a characteristic of the skin region. The step of applying radiation can further include applying radiation at a plurality of wavelengths selected from a range of about 350 nm to about 1200 nm, or in a range of about 600 mm to about 900 mm, to the skin. In addition, optical contact between the waveguide and the skin region can be detected. Contact of the waveguide with the tissue can be sensed by detecting a level of the backscattered radiation. The method can further include reducing ambient radiation to prevent its detection by the detector. In some embodiments, the method further can include reducing radiation having a first polarity prior to detection; and detecting radiation having a second polarity.

DETAILED DESCRIPTION

The present invention relates generally to diagnostic and/or therapeutic dermatological and other devices, as well as diagnostic and therapeutic methods, that determine one or more characteristics of the skin by analyzing radiation scattered by the skin in response to its illumination at least one wavelength, and more preferably, at two or more wavelengths. In other aspects, the invention provides optical sensors for determining whether an optical element, such as a waveguide or treatment window through which radiation from a device is transmitted to the skin, is in contact with the skin.

Figure 1A:
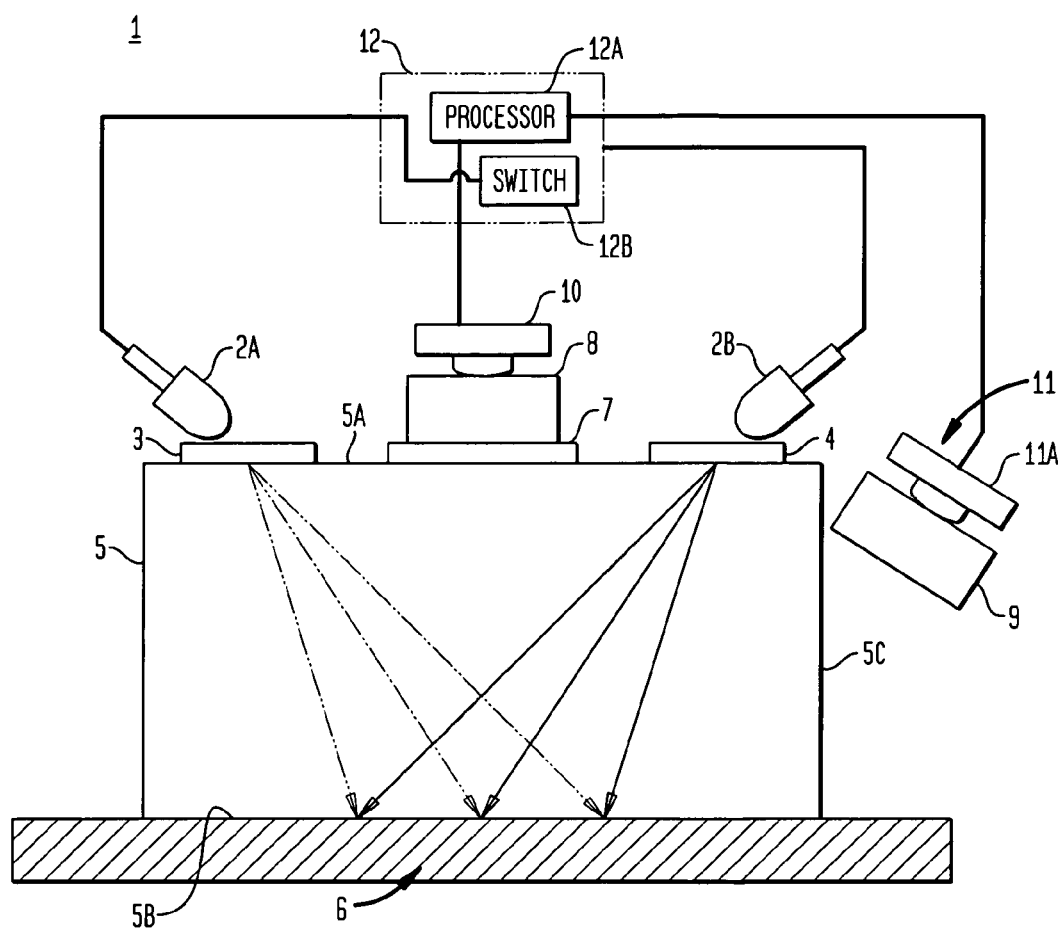
FIG. 1A is a schematic side view of a dermatological device in accordance with one embodiment of the invention.

FIG. 1A schematically depicts a cross-sectional view of an exemplary dermatological device 1 in accordance with one embodiment of the invention that measures a physical property of tissue, the melanin optical density ("MOD") of human skin in this particular embodiment. Device 1 includes two light sources 2A and 2B that generate radiation having different wavelengths selected to be sufficiently separate to provide two independent measures of the physical characteristic.

Depending on the application, various wavelengths can be used. In this case, for the measurement of MOD, many different wavelengths can be selected, but the wavelengths preferably are in a range of about 600 nm to about 900 nm, though wavelengths in other ranges can also be employed. (The terms "light" and "radiation" are herein used interchangeably to refer to electromagnetic radiation within a desired spectral range. Unless otherwise specified, these terms are used as examples, and it should be understood that other forms of radiant energy can be used depending on the application, including acoustic energy, ultrasound, microwaves, infrared, visible light and other electromagnetic radiation.)

Generally, the separation of the wavelengths is selected so as to elicit a sufficient differential response at those wavelengths from a skin chromophore (e.g., melanin) so as to allow accurate measurements of that chromophore's concentration in the skin. By way of example, in this embodiment, source 2A generates radiation at a wavelength of about 645 nm, while source 2B generates radiation at a wavelength of about 700 nm. This choice of the wavelengths is particularly suited for measuring the skin melanin content, as it provides adequate differential response from melanin while minimizing optical interference from other skin components, such as blood or water.

A variety of coherent or incoherent radiation sources can be utilized as sources 2A and 2B. For example, in some embodiments, the sources 2A and 2B include light emitting diodes (LEDs) while in others, they can include laser diodes, lamps, etc. In still other embodiments, a single source can be used to produce both wavelengths of light by, for example, passing light from an incoherent source through one or more filters. Similarly, a single source could be used to provide radiation across one or more bands of radiation, while the desired wavelengths within the band are detected using sensors sensitive to those wavelengths.

The use of LEDs in this exemplary embodiment provides a number of advantages. For example, LEDs are typically low cost, compact and reliable radiation sources. Further, their light output can be controlled and modulated precisely. In addition, the profiles of their output radiation beams can be controlled, e.g., by utilizing molded lenses. It should, however, be understood that any other suitable radiation source can also be employed.

The light sources 2A and 2B are optically coupled to a waveguide 5 via a top surface 5A thereof such that at least a portion of the light generated by each source enters the waveguide for transmission to a subject's skin. Waveguides are well known in the art of optics, and generally refer to any optically transmissive medium that provides an optical path from a first location to a second location through the medium. As discussed in more detail below, the radiation entering the waveguide is transmitted by the waveguide to a surface 5B thereof through which, upon contact of that surface with the skin, the radiation is transmitted to a skin region 6. A portion of the radiation illuminating the skin is specularly reflected by the skin surface, and another portion enters the skin.

As the skin is a turbid medium, the radiation entering the skin undergoes multiple scattering and/or reflection events, which result in re-entry of some of the radiation back into the waveguide (that is, some of the radiation is backscattered into the waveguide). The waveguide 5 can advantageously function similarly to an optical integrating sphere to allow a substantially uniform illumination of a skin segment of interest, and can facilitate coupling of the backscattered radiation to a detector 10. The detector 10 is optically coupled to the surface 5A of the waveguide to receive at least a portion of the backscattered radiation that is coupled from the skin into the waveguide, via the waveguide's surface 5B. At least a portion of the backscattered radiation is coupled of out of the waveguide through the surface 5A to be detected by the detector. A variety of optical radiation detectors known in the art can be employed. An example of such a detector includes a commercially available detector marketed by Hamatsu as serial number 56865-01.

As such, the waveguide can allow repeatable optical coupling between the device and the skin. As discussed in more detail below, poor coupling between the device and the skin can lead to inaccurate measurements due to dramatic changes in light coupling, transmission and diffusion. Furthermore, in device 1, the waveguide medium is a substance, in this case, sapphire or other suitable medium, such as fused silica or glass, that has an index of refraction sufficiently different than air to, as discussed in greater detail below, utilize the concept of total internal reflection to achieve the desired measurement of MOD. (However, as will be evident in additional embodiments described below, other media, including substances having an index of refraction close to that of air or even air itself, may be used as a waveguide. For example, a hollow reflective tube containing a fluid such as air or configured to secure a liquid, could be used as a waveguide in some embodiments.)

Device 1 further includes polarizers 3 and 4, which have parallel polarization axes which are placed between the light sources 2A and 2B, respectively, and the surface 5A of the waveguide 5. Another polarizer 7, having a polarization axis perpendicular to that associated with polarizers 3 and 4, is placed between detector 10 and the surface 5A of the waveguide 5. The purpose of the polarizers 3, 4 and 7 is to remove light reflected from the surface of the tissue and other surfaces and that does not, therefore, penetrate into the tissue. This arrangement of polarizers ensures that the radiation that is specularly reflected from various interfaces (e.g., waveguide/air, waveguide/skin, air/skin, or waveguide/lotion, air/lotion (in cases where lotion is applied to the skin)) is substantially inhibited from reaching the detector 10. Such specularly reflected radiation has the same (or at least substantially the same) polarization as that of the polarized radiation from the sources, and hence is blocked by the orthogonal polarizer coupled to the detector. The use of this arrangement of polarizers is particularly advantageous in preventing the radiation that is specularly reflected from the skin surface from reaching the detector. The specularly reflected radiation does not penetrate the skin and hence it typically does not contain any information regarding the skin pigment of interest. Its blockage from the detector 10 increases the accuracy of the measurement. In contrast, the information regarding the skin pigment of interest is carried mostly by the light that is diffusely backscattered by the dermis layer of the skin. As this diffusely scattered light exhibits random polarization, a portion of the light having the opposite polarization from the specularly reflected light can pass through the polarizer 7 to be detected by the detector 10. Thus, the light that reaches detector 10 is predominately light that provides information about the physical characteristic being measured, in this case the MOD of the tissue.

In addition, device 1 contains a spectral filter 8 between polarizer 7 and detector 10. This filter passes the desired wavelengths emitted by sources 2A and 2B, but filters out other sources of radiation noise (e.g., ambient light and radiation from the treatment source), thereby enhancing the measurement sensitivity of the device.

With continued reference to FIG. 1A, the device 1 further includes an optical contact sensor 11, comprising a radiation detector 11A and a filter 9, that is optically coupled on one side to detector 11a and to the waveguide 5 via a sidewall 5C thereof (which extends between the surfaces 5A and 5B), to detect contact between the waveguide (and more particularly between the surface 5B of the waveguide through which the radiation is transmitted to the skin) and the skin. The terms "contact" and "optical contact," as used herein, refer not only to physical contact but also sufficient proximity between a surface of the waveguide and the skin that would result in detection of a signal by the sensor above a predefined threshold.

In particular, the detector 11 detects a portion of the radiation that enters the waveguide through the surface 5B and exits the waveguide through the sidewall 5C. When the optical coupling between the surface 5B and the skin surface is poor (e.g., when a substantial air gap is present between that surface and the skin) the amount of radiation that is leaked from sidewall 5C is low, and, thus, detector 11 detects a low signal. When the optical coupling between the surface 5B and the skin surface is good (e.g., when little or no gap exists between surface 5B and tissue 6 or when full contact is achieved between the tissue 6 and the surface 5B) the amount of radiation that is leaked from sidewall 5C is substantially increased, and, thus, detector 11 detects a high signal.

The difference in the two signals is due to the total internal reflection of the light due to the difference in the indices of refraction of the waveguide and the air. The waveguide has an index of refraction that is significantly greater than that of the air, approximately 1.45 to 1 respectively. Thus, in operation, the bulk of the radiation emitted from sources 2A and 2B will exit the waveguide via surface 5B, and only a small portion will be reflected internally, and only a small portion of that reflected radiation will exit sidewall 5C. When the surface 5B is oriented toward the tissue 6, some of the emitted light will be reflected back to the device. The differences in the indexes of refraction, however, cause the light to refract upon reentry into waveguide 5 at angles that subsequently cause substantially all of the light to be totally internally reflected, such that essentially none of the light exits surface 5c.

When the device is touching the tissue, substantially more light reenters the waveguide 5 and passes through surface 5C. Thus, detector 11 then detects a significantly greater amount of light, thereby indicating that contact has been made (or that the device is positioned sufficient close to obtain a reading of MOD). The detector 11A of the sensor 11 indicates the presence of optical contact between the waveguide and the skin when its detection signal exceeds a pre-defined threshold, and it indicates the absence (or poor) optical contact between the waveguide and the skin when the detection signal is less than that threshold.

Figure 1B:
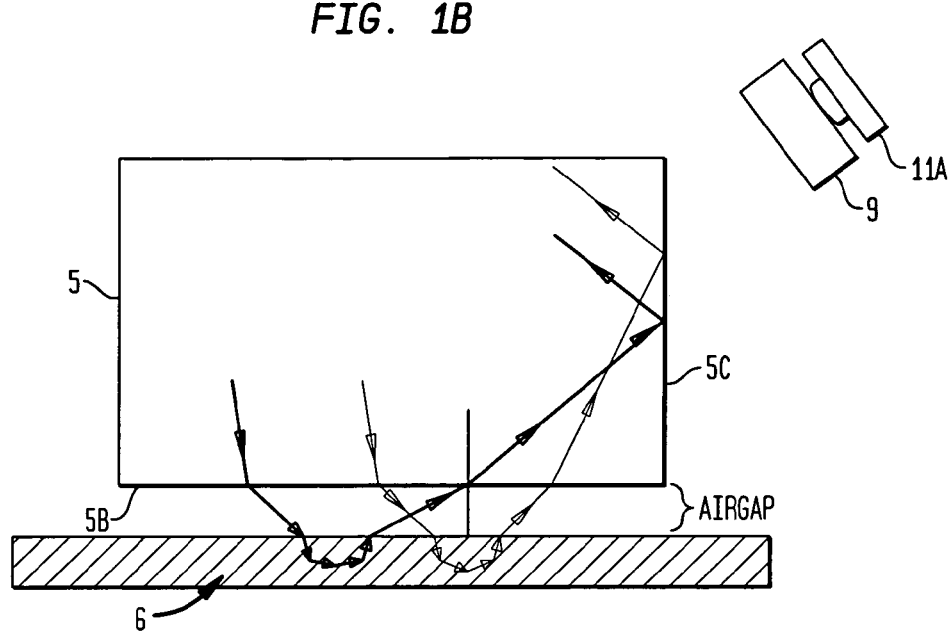
FIG. 1B schematically shows that in the absence of contact between a waveguide of the device of FIG. 1A and the skin, a substantial number of radiation rays backscattered from the skin into the waveguide are totally internally reflected at the waveguide's sidewall to which an optical sensor is optically coupled, thus resulting in a low detection signal by the sensor.
Figure 1C:
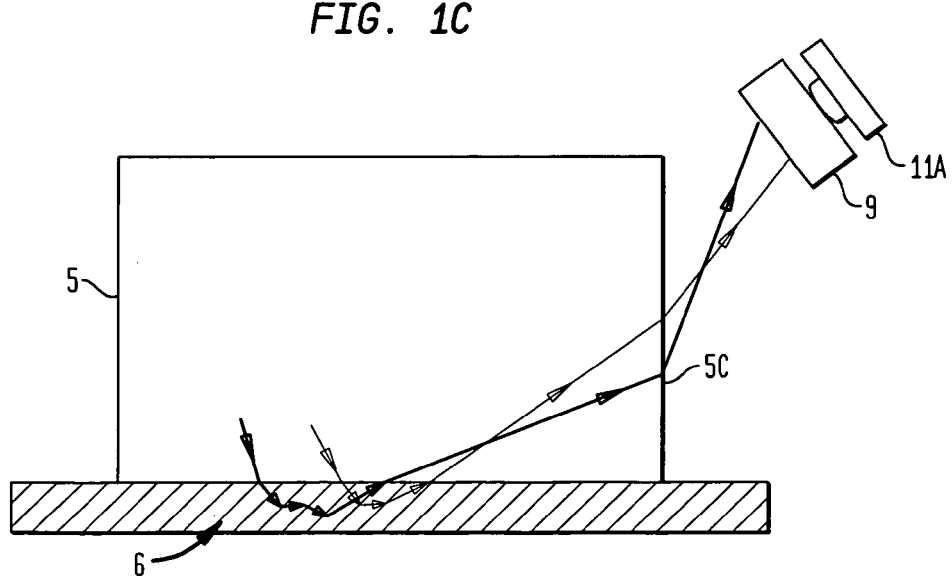
FIG. 1C schematically shows that in the presence of contact between the waveguide of device of FIG. 1A and the skin, a substantial number of radiation rays backscattered from the skin into the waveguide to be incident on a sidewall of the waveguide to which an optical sensor is coupled are transmitted through the sidewall to reach the sensor, thus resulting a sensor signal above a threshold that indicates contact.
Figure 1D:
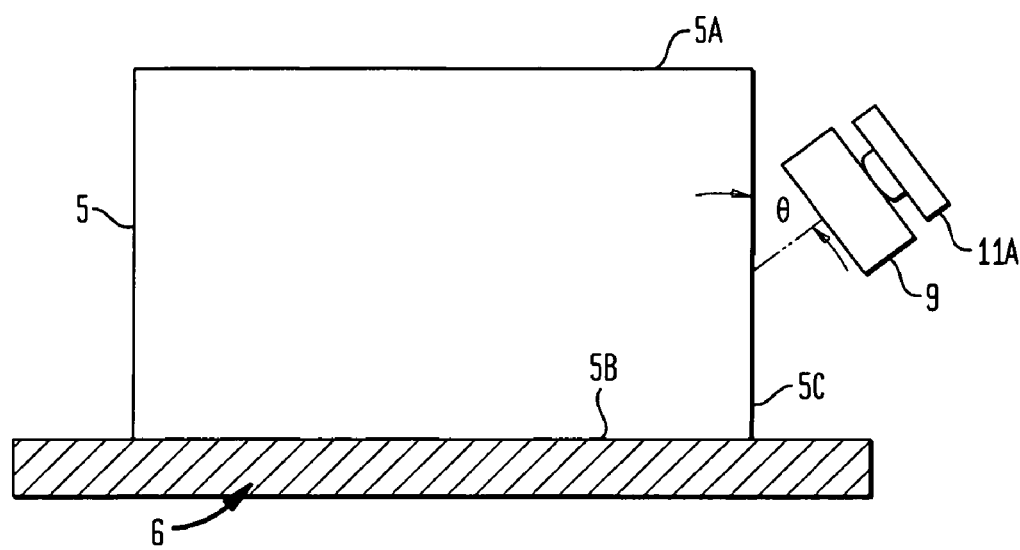
FIG. 1D schematically shows that the detector of an optical sensor coupled to a sidewall of a waveguide of the device of FIG. 1A is positioned relative to the sidewall such that a central ray corresponding to the detector's viewing solid angle makes an angle φ relative to the sidewall selected to ensure that in the absence of contact between the waveguide and the skin, the radiation rays backscattered from the skin into the waveguide are substantially inhibited from reaching the detector and, in presence of contact, some of those rays exit the sidewall to reach the detector.
Figure 1E:
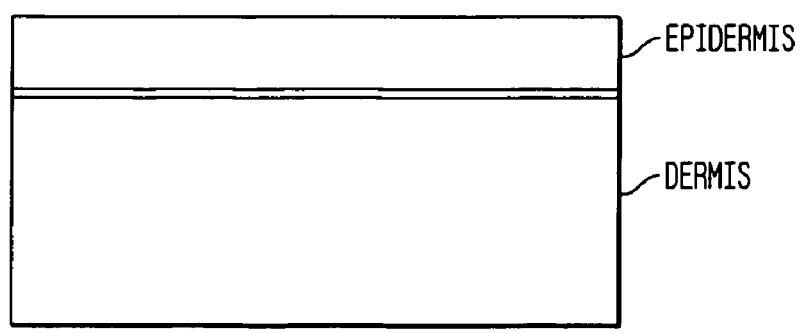
FIG. 1E schematically depicts a skin portion comprising an epidermis layer, a dermis layer and an epidermis/dermis junction exhibiting a high concentration of melanin.
Figure 1F:
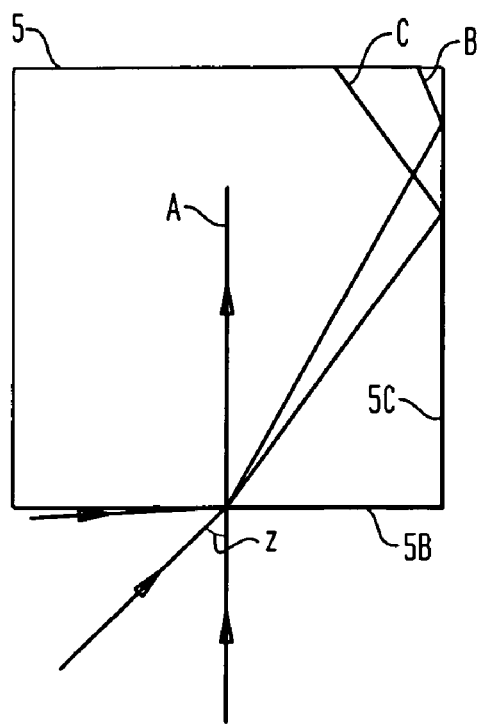
FIG. 1F is a schematic diagram of rays of radiation entering a waveguide from the air at various angles.
Figure 1G:
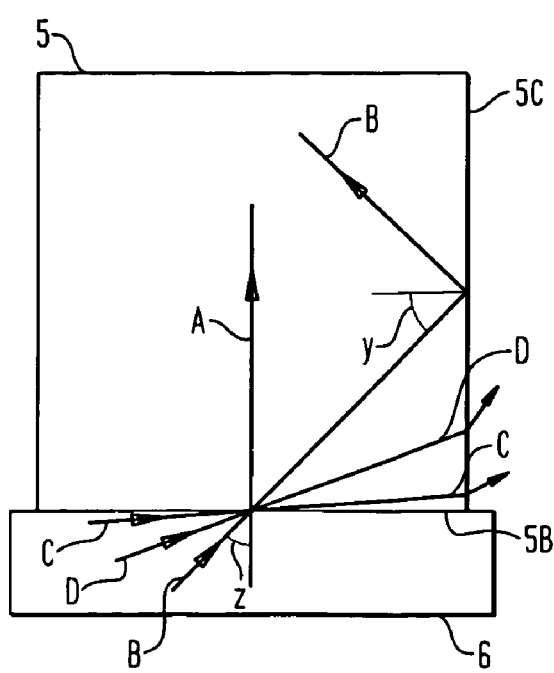
FIG. 1G is a schematic diagram of rays of radiation entering a waveguide from skin tissue at various angles.

The principle is illustrated in FIGS. 1F and 1G. FIG. 1F shows the condition where the waveguide 5 is not in contact with the tissue. Thus, the medium that the rays of light a, b and c travel through prior to entering the waveguide is air, which has an index of refraction of approximately one (n=1), while the index of refraction of the waveguide is approximately 1.45. Thus, as shown in greater mathematical detail below, any ray traveling within the waveguide that strikes a waveguide/air boundary at an angle that is larger than 43.6 degrees (the critical angle, which is measured relative to a normal line extending from surface 5c) will be totally internally reflected. However, as illustrated in FIG. 1F, all radiation that reenters the waveguide will be refracted to an angle that is larger than the critical angle relative to surface 5c. For example, ray a, which is normal to the air/waveguide boundary, travels in a straight line and parallel to surface 5c. Ray b strikes the air/waveguide boundary at an angle of incidence of 46.4 degrees from the normal relative to surface 5b, but is refracted to a steeper angle relative to surface 5c and is totally internally reflected. Similarly, ray c, which is nearly parallel to the air/waveguide boundary, is also refracted: to an angle slightly greater than the critical angle of 43.6 degrees relative to a line normal to surface 5c. Thus, ray c is also totally internally reflected.

In the case where the waveguide 5 is in contact with the tissue 6, as shown in FIG. 1G, any light that strikes the tissue/waveguide boundary at an angle of incidence greater than z (46.4 degrees) will not be totally internally reflected at the surface 5c. In this example, the indices of refraction of the tissue and the waveguide are approximately the same (n=1.45). Therefore, the light will not refract significantly, and will continue to travel in an essentially straight line. Thus, any radiation having an angle of incidence greater than approximately angle z will not be totally internally reflected. As shown in FIG. 1G, rays c and d are not totally internally reflected. Ray b, which has an angle of incidence on surface 5c at the critical angle y (43.6 degrees), is totally internally reflected. Any ray incident at a smaller angle than 43.6 degrees will not be totally internally reflected. Any ray incident at a larger angle than 43.6 degrees will be totally internally reflected.

Of course, many other embodiments are possible, including, without limitation, embodiments where the reverse is true, i.e., the light is totally internally reflected until contact is made, thus causing the level of light detected to drop significantly when contact is made. Thus, contact may be signaled when the light level drops below a defined threshold. Additionally, although it is preferable to use a waveguide having an index of refraction that is matched or nearly matched to that of the tissue, it is not essential. Alternate embodiments can be designed having indices of refraction that are not matched. For embodiments used on the surface of the skin, it is preferable, though not essential, to use a lotion to facilitate the transfer of radiation from sources 2A and 2B to the skin, and even more preferable to use a lotion with an index of refraction that is matched to or nearly matched to the refractive index of the skin. Other tissues may not require a lotion, especially tissues such as those of the oral cavity that may already be coated with natural moisture that will facilitate the transfer of light or other radiation.

With reference to FIGS. 1B and 1C, the functionality of the optical sensor 11 can be further understood by considering the geometry of total internal reflection in greater detail in two cases: the case in which the waveguide 5 is not in contact with the skin (FIG. 1B showing that an air gap separates the surface 5B of the waveguide and the skin) and the case in which the waveguide is in full contact with the skin (FIG. 1C). In the first case, a portion of the radiation from the sources that travels through the waveguide is specularly reflected by the waveguide/air interface and another portion enters the air gap and passes therethrough to strike the skin. The radiation rays reflected and/or scattered by the skin back towards the waveguide pass through the air gap and strike the surface 5B of the waveguide. Some of the light will enter the waveguide, but does so at angles (again, due to refraction at the waveguide-air interface) that in most cases result in their total internal reflection at the sidewall 5C.

When surface 5b is in air, the angle of incidence (φ) of a ray A incident on the surface 5c can be equal or greater than the minimum angle at which total internal reflections occurs, as indicated by the following relation:

$$\phi \geq \arcsin(n_m/n_w) \quad \text{Eq. (1)}$$

wherein, $n_m$ denotes the index of refraction of the medium (e.g., air) surrounding the waveguide, and.

$n_w$ denotes the index of refraction of the material forming the waveguide.

In contrast, when the surface 5B is in contact with the skin (FIG. 1C), the back-scattered radiation rays entering the waveguide strike the sidewall at angles that allow a substantial number of those rays to leave the waveguide to reach the sensor.

In many embodiments, in order to optimize the performance of the sensor, the index of refraction of the material forming the waveguide is selected to be significantly different than the index of refraction of the air. Preferably, the material forming the waveguide exhibits an index of refraction close to that of the skin, approximately n=1.45. In the present embodiment, the waveguide is made of fused silica having an index of refraction of approximately 1.45. In other embodiments, different media may be used, for example, sapphire, which has an index of refraction of approximately 1.7.

Further, as shown schematically in FIG. 1D, the detector 11 is preferably placed relative to the sidewall of the waveguide such that a central ray A in a solid angle corresponding to the detector's field-of-view forms an angle θ of approximately 30 degrees relative to the sidewall 5C. Other angles are possible, and will vary depending on the physical properties of the materials involved, including the material of the waveguide, the tissue involved (skin, oral tissue, and other tissues), and the material between the waveguide and the tissue (air, water, blood, etc.). Each will have a different index of refraction, and thus will result in different values for the optimal angle of the detector 11A. In some such embodiments, it may be preferable to include an additional prism on the surface (e.g., surface 5c in FIG. 1A), such as a right angle fused silica prism.)

Referring again to FIG. 1A, the device 1 further includes a feedback mechanism 12 in communication with the optical sensor 11, the detector 10, as well as the sources 2A and 2B. The feedback system 12 ignores the output signal from detector 10 when the optical sensor indicates no or poor optical contact between the waveguide (e.g., in this embodiment, between the surface 5B of the waveguide) and the skin. During operation, however, sources 2A and 2B will be on continuously or engaged at regular intervals to check for contact. (In some embodiments, the source or sources that provide the radiation to measure a physical characteristic of the skin may also provide additional radiation for other purposes, such as treatment or diagnosis. In such embodiments, the feedback system will control the source or sources to ensure that other radiation is provided at the proper time, depending on the detection of contact.)

More specifically, in this embodiment, the feedback system 12 includes a processor 12A that receives the output signals of the detector 11A of the sensor. The processor compares the detector's output signal with a pre-defined threshold to determine whether an appropriate optical contact exists between the waveguide's surface 5B and the skin (a detector signal that is less than the threshold indicates no optical contact between the waveguide and the skin). If the output signal of the sensor's detector is less than the threshold, the processor ignores the output of detector 10, or, alternatively, may inhibit operation of the device such that no measurement of a physical characteristic of the tissue or treatment of the tissue is provided. For example, in this embodiment, the processor 12A can send control signals to a switching unit 12B that, in turn, ignores the output of detector 10. Sources 2A and 2B will always be engaged (either continuously or periodically) because they provide the radiation that is detected by the detector 11A to determine if the system is in contact with the tissue. (Alternatively, a separate light source could be provided that provides radiation to be detected by detector 11A, and thereby allow sources 2A and 2B to be engaged only when measuring a physical characteristic of the tissue.)

As discussed in more detail below, the processor 12A also operates on the output signals received from the detector 10 to determine a skin characteristic of interest. In other embodiments, the sensor 11 has its own dedicated processor that operates on the output signal of the sensor's detector 11A to determine whether or not the waveguide is in optical contact with the skin, and sends that information to the feedback system 12.

With continued reference to FIG. 1A, as noted above, the processor 12A can also analyze the signals generated by the detector 10, in response to detection of the backscattered radiation from the skin illuminated by the radiation generated by the sources 2A and 2B, to determine a skin characteristic of interest, such as the concentration of melanin in the skin. The term "backscattered radiation," as used herein refers to radiation that returns from the illuminated skin to the waveguide via reflection and/or scattering events.

By way of example, the device 1 can be employed in the following manner to determine the melanin concentration in a skin segment. For example, the sources 2A and 2B can be sequentially activated to illuminate a skin segment that is contact with the waveguide after the optical sensor 11 detects optical contact between the waveguide's surface 5B and the skin. The sources can provide the radiation at wavelengths of 645 nm and 700 nm in different temporal intervals. A portion of the radiation illuminating the skin penetrates the skin and passes through the epidermis to reach the dermis via passage through the dermis/epidermis junction (DE junction). As the skin is a turbid medium, the radiation entering the skin undergoes many scattering and/or reflection events, especially in the dermis layer. Some of the radiation is absorbed by melanin, particularly as it passes through the dermis/epidermis junction, at which the melanin concentration is high in this example. The multiple scattering/reflection events cause some of the radiation to be coupled out of the skin back into the waveguide.

Due to the absorption characteristics of melanin, a relatively high level of light will be backscattered to waveguide 5, if the skin contains a relatively low amount of melanin. Conversely, a relatively low level of light will be backscattered to waveguide 5 if the skin contains a relatively high amount of melanin. As a result of the interaction of the radiation entering the skin with melanin, the radiation that is backscattered into the waveguide, therefore, carries information regarding the MOD.

By way of example and without being limited to any particular theory, the intensity of the radiation backscattered from the skin into the waveguide at each of the two illumination wavelengths utilized in this embodiment can be characterized by the following relation:

$$R_d^\lambda = \kappa(T_\lambda^2 R_{dermis}) \qquad \text{Eq. (2)}$$

wherein, $R_d^\lambda$ denotes diffuse reflectance (backscattered radiation intensity) from the skin region illuminated with radiation at wavelength $\lambda$, $\kappa$ is a proportionality constant that can depend, e.g., on the intensity of the illuminating radiation as well as geometrical factors associated with coupling of the radiation into the skin, $T_\lambda$ is the transmission coefficient through the skin at the illumination wavelength $\lambda$, which depends on the melanin concentration, and $R_{dermis}$ denotes diffuse reflectance from the dermis.

The transmission coefficient $T_\lambda$ depends on the concentration of melanin in the illuminated skin region, as melanin can absorb some of the radiation. Hence, $R_d^\lambda$ carries information regarding melanin concentration. In this exemplary embodiment, the radiation wavelengths are selected to be in a range of about 600 nm to about 900 nm to ensure that the interaction of the radiation with blood is minimal. As such, the above Eq. (2) does not take into account the contributions of blood.

The apparent optical density ($OD_\lambda$) of the illuminated skin at an illumination wavelength ($\lambda$) can be determined from the following relation:

$$OD_\lambda = -\log R_d^\lambda \qquad \text{Eq. (3)}$$

As the above transmission coefficient $T_\lambda$ is proportional to melanin optical density at wavelength $\lambda$ (referred to as $OD_\lambda^{mel}$), Eq. (3) can be rewritten in the following manner:

$$OD_\lambda = OD_\lambda^{mel} - \log R_{dermis} \qquad \text{Eq. (4)}$$

The selection of the radiation wavelengths in a range of about 600 nm to about 900 nm ensures that while $T_\lambda$ is wavelength dependent, $R_{dermis}$ is substantially independent of the illumination wavelength. As such, the difference between apparent optical density ($OD_\lambda$) at two wavelengths, and more generally the slope of apparent optical density in the spectral range of about 600 nm to about 900 nm, is proportional to the melanin concentration. For example, a melanin index (M) can be defined in the following manner:

$$M = 100(OD_{\lambda_1} - OD_{\lambda_2}) \qquad \text{Eq. (5)}$$

By way of example, in many embodiments, the processor 12A employs the above mathematical relations to calculate the melanin optical density based on the detected intensity of the radiation diffusely reflected (backscattered) from the skin.

Figure 2:
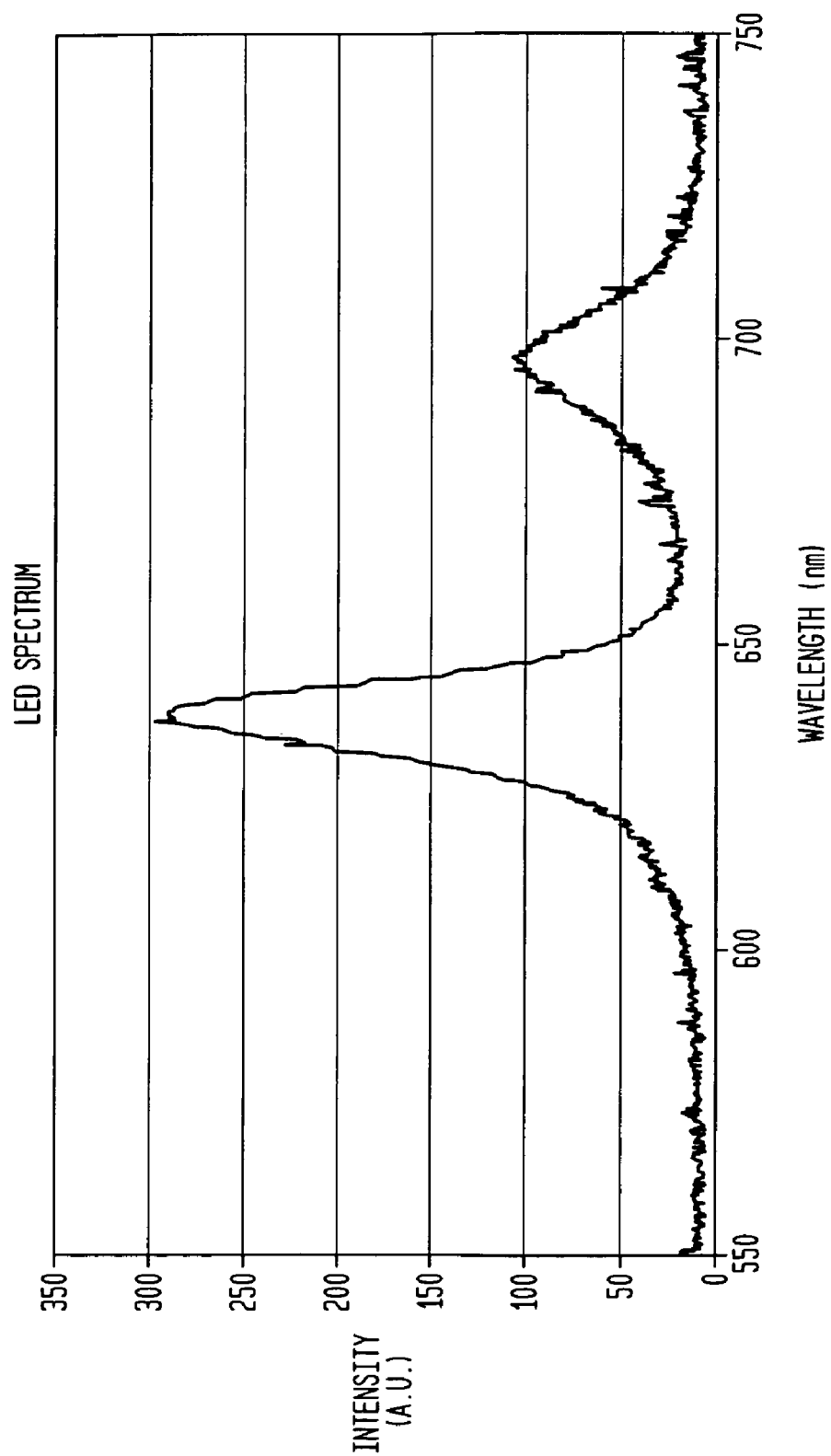
FIG. 2 depicts the emission spectra associated with two exemplary LEDs suitable for use in some embodiments of the invention.
Figure 3:
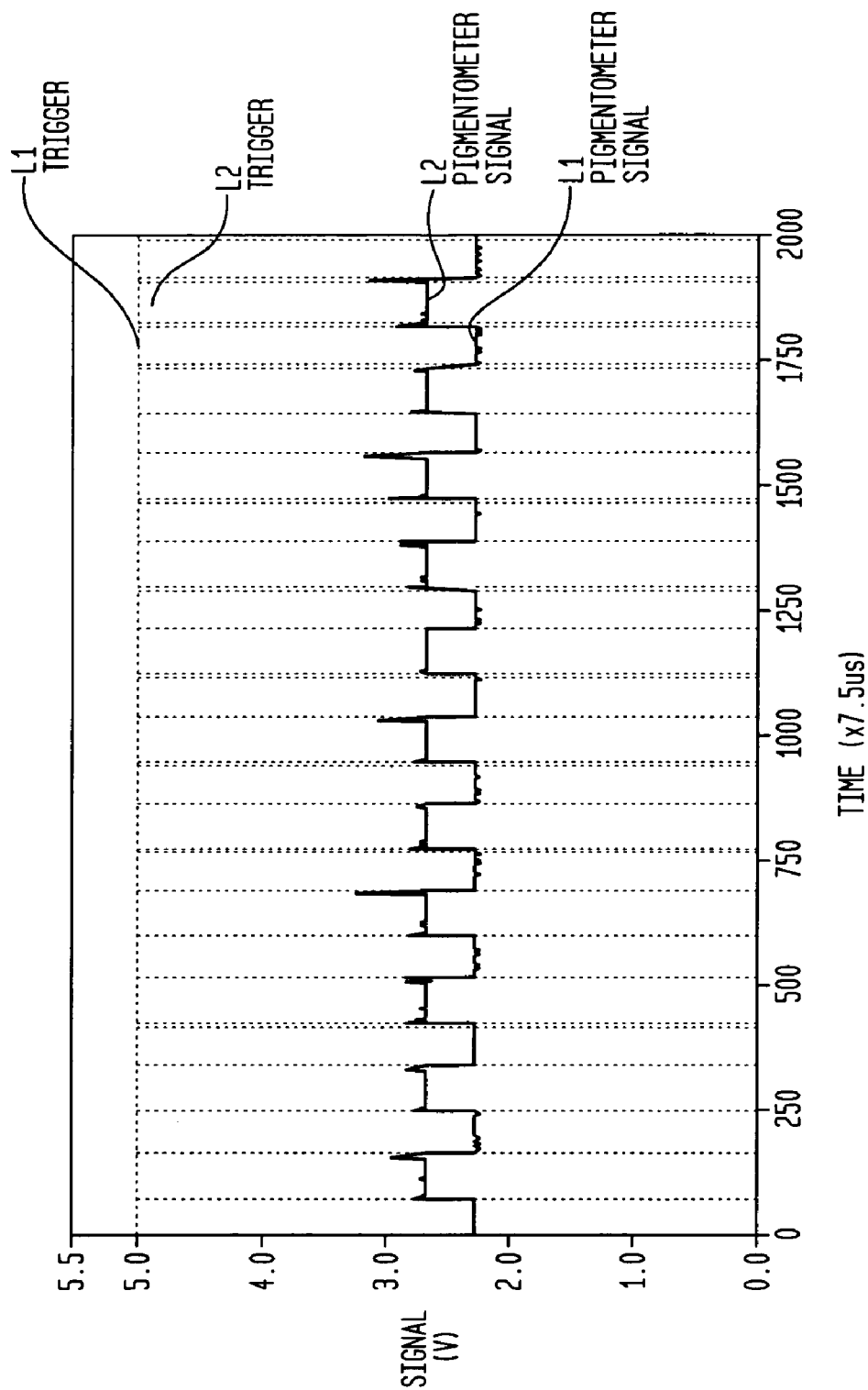
FIG. 3 depicts trigger signals applied to the LEDs forming radiation sources in an embodiment of the invention as well as the backscattered signals detected for illumination of a skin portion with radiation generated by those LEDs.

By way of illustration and only for the purpose of showing the efficacy of the systems and methods of the invention for measuring the skin melanin optical density, a prototype device was constructed according to the teachings of the invention. A comparison of melanin measurements performed by that device on a number of subjects with corresponding measurements performed by a few conventional devices on the same subjects showed that the prototype device provides enhanced performance, particularly significantly better measurement repeatability. The radiation spectrum of the two LEDs utilized in the prototype device is shown in FIG. 2. While one LED exhibits a maximum radiation intensity at a wavelength of about 645 nm, the other LED has a maximum radiation intensity at a wavelength of about 700 nm. FIG. 3 provides raw signal generated by the detector measuring backscattered radiation for determining melanin concentration (referred to in the figure as "pigmentometer signal") in response to triggering of the LEDs in different time intervals. The raw data can be analyzed, e.g., in a manner discussed above, to arrive at the melanin index.

Figure 4:
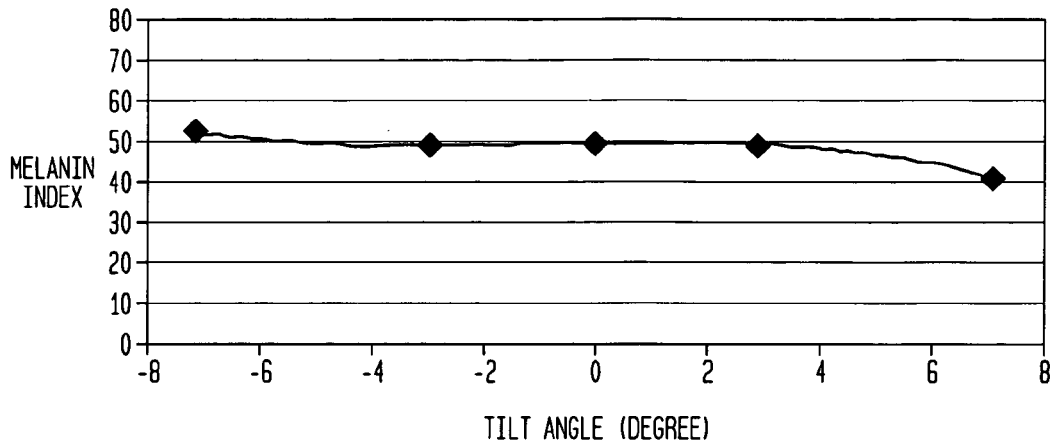
FIG. 4 shows the signal sensitivity of an exemplary, illustrative device according to an embodiment of the invention for measuring the melanin index as a function of tilt angle relative to the skin under observation.
Figure 5:
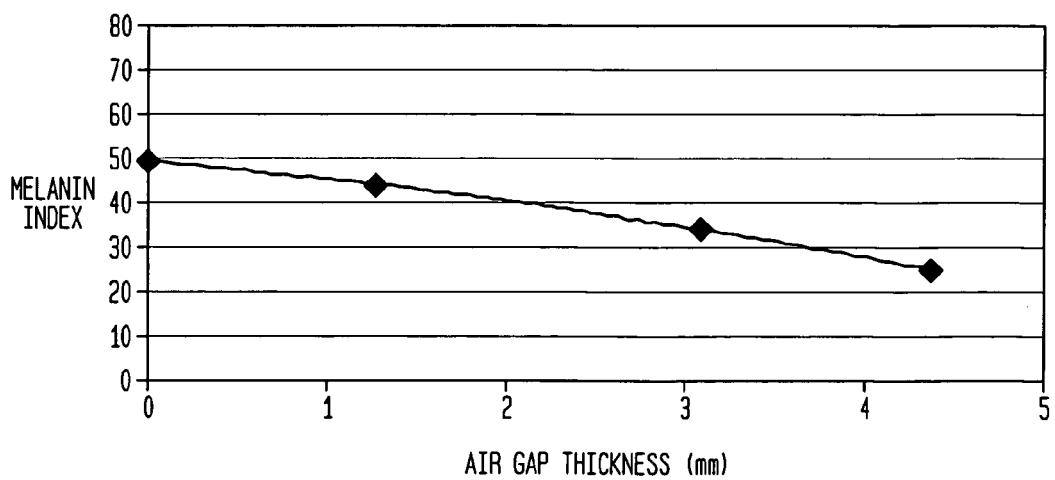
FIG. 5 shows the signal sensitivity of an exemplary, illustrative device according to an embodiment of the invention for measuring the melanin index as a function of the thickness of an air gap between a surface of a device adapted for contact with the skin and a skin portion under observation.

By way of further illustration, in another device similar to the prototype discussed above in which the wavelengths used were 660 and 910 nm respectively, FIG. 4 shows the sensitivity of the device as a function of its tilt relative to the skin (rocking sensitivity) and FIG. 5 shows the sensitivity of the device as a function of the thickness of air gap between the device and the skin. It should be understood that the data is presented only for illustration purposes, and is not intended to necessarily indicate the optical signal intensities that can be obtained by a device of the invention. Many other embodiments are possible, and the data provided is specific to the prototype devices that were tested, which were similar in design to the embodiment described in conjunction with device 1.

Figure 6:
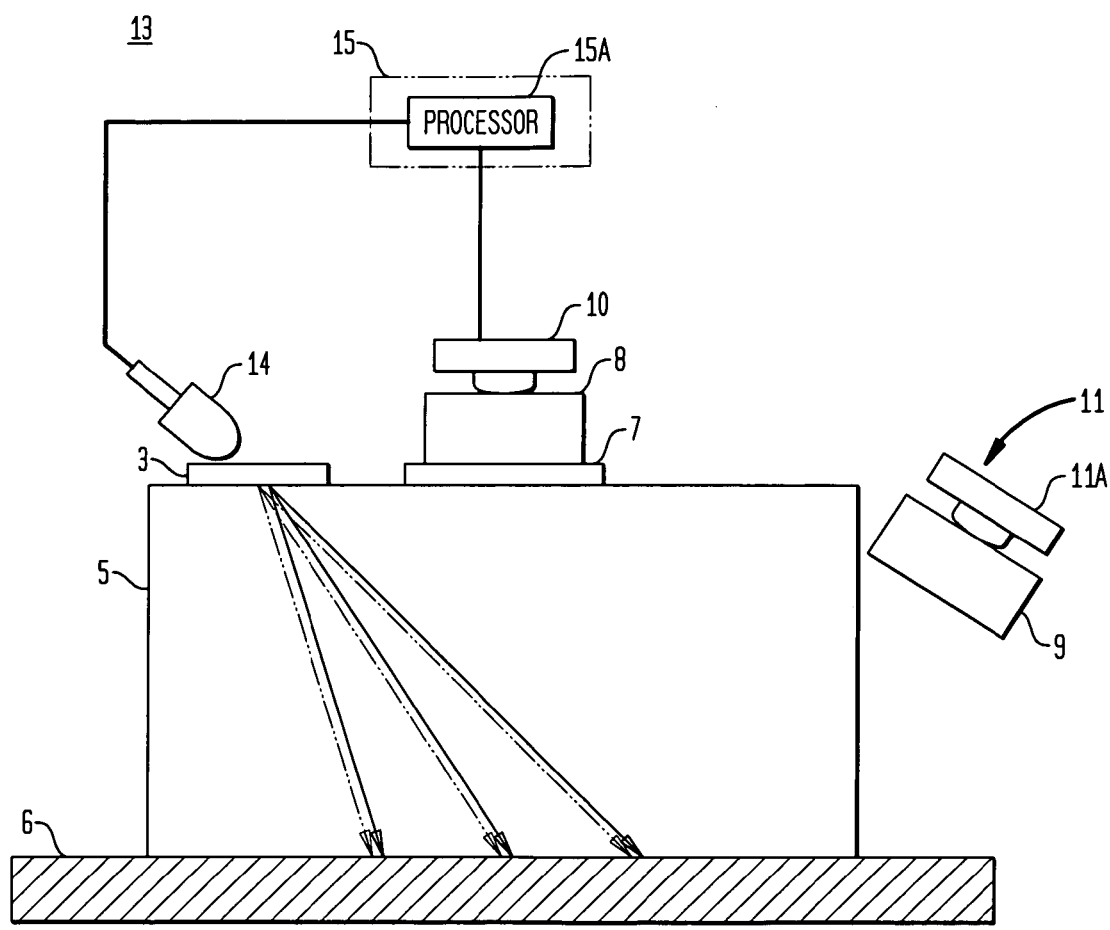
FIG. 6 is a schematic side view of a dermatological device according to another embodiment of the invention that employs a single radiation source capable of generating radiation at two or more wavelengths in a wavelength range of interest.

Although in the above embodiment, two sources, each of which generates radiation at a different wavelength, are employed, in some other embodiments, a single source generating radiation at two or more different wavelengths can be employed. To measure MOD, the sources preferably emit radiation in a range of about 600 nm to about 900 nm. By way of example, as shown schematically in FIG. 6, a dermatological device 13 includes a single radiation source 14 capable of generating radiation at two or more wavelengths, e.g., a bicolor light emitting diode (bicolor LED), that is capable of generating radiation at two or more wavelengths in a range of about 600 nm and about 900 nm. Again, the wavelengths 645 and 700 are thought to be preferable, but many other combinations of wavelengths are possible.

Device 13 further includes a control unit 15 having a processor 15a can actuate the bicolor LED 15 so as to generate the color of interest. For example, the control unit can cause the LED to generate the various wavelengths in different temporal intervals for illuminating a skin region of interest. More specifically, similar to the previous embodiment, the radiation generated by the LED 15 is optically coupled to a waveguide 5 via passage through a polarizer 3. The waveguide 5 transmits the radiation to tissue 6, in this case human skin. A detector 10 that is optically coupled to waveguide 5 via a filter 8 and polarizer 7, receives at least a portion of the radiation that is diffusely back-reflected (backscattered) from the illuminated skin. Similar to the previous embodiment, the detector 10 is coupled to the polarizer 7 having a polarization axis orthogonal to that of the polarizer 3 to suppress, and preferably eliminate, the detection of specularly reflected radiation, especially specular reflections at the surface of the illuminated skin, by the detector 10. Further, the filter 8 prevents ambient radiation noise, e.g., due to artificial ambient lighting units, from reaching the detector 10.

The processor 15a receives the output signals generated by the detector 10, in response to illumination of the skin at two or more wavelengths, and analyzes those signals, e.g., in the manner discussed above, to determine a physical characteristic of the skin such as the MOD. Further, similar to the previous embodiment, the device 13 includes an optical sensor 11 having a detector 11a optically coupled to a filter 9, which can determine whether the waveguide is in contact with the skin, also in a manner similar to the detector 11 as described in conjunction with FIG. 1A.

Figure 7A:
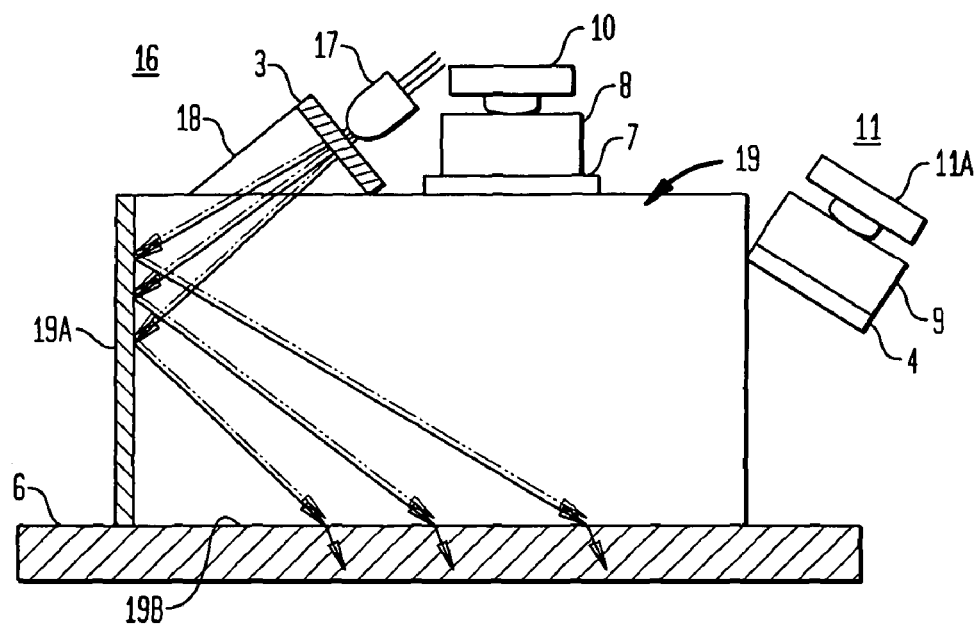
FIG. 7A schematically depicts a dermatological device in accordance with another embodiment of the invention that utilizes a waveguide having a reflective sidewall for coupling radiation from a source into the skin.
Figure 7B:
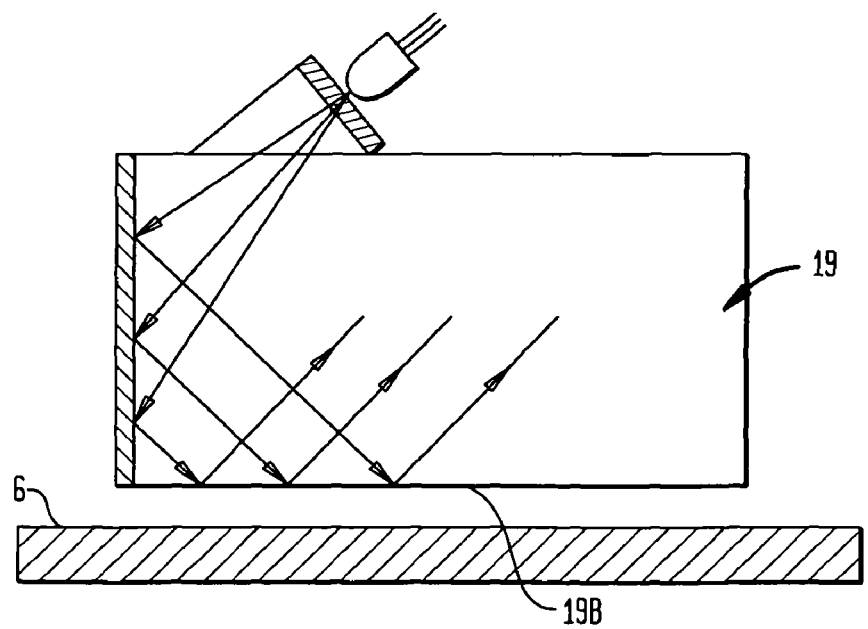
FIG. 7B schematically shows that the reflective sidewall of the waveguide of the device of FIG. 7A directs radiation received from the source to a surface of the waveguide adapted for contact with the skin such that in the absence of contact, the radiation is totally internally reflected from that contact surface.

The embodiments of a device according to the teachings of the invention are not limited to those discussed above. For example, FIG. 7A schematically depicts a dermatological device 16 according to another embodiment of the invention that includes a radiation source 17 whose radiation is coupled via a prism 18 to a waveguide 19. Similar to the previous embodiments, a polarizer 3 is coupled to the source 17 and polarizes the source radiation. (Though many materials are possible, the prism in this embodiment is made of $CaF_2$.) The waveguide 19 includes a reflective sidewall 19a that reflects the radiation entering the waveguide to a waveguide surface 19B that is adapted for contact with the skin. The waveguide 19 can be, for example, a block formed of a material, such as fused silica, having an index of refraction that is preferably close to that of the skin, and reflective sidewall can be formed, e.g., by coating a reflective material (such as silver) on a waveguide surface. In this embodiment, the source 17 and the prism 18 are positioned relative to the waveguide such that the radiation rays entering the waveguide are reflected by the sidewall 19a to tissue 6. The reflected radiation strikes the skin/waveguide interface at surface 19B at an angle of incidence (AOI) that, in the absence of optical contact between the surface 19B and the skin, results in total internal reflection (TIR) of those rays, thus preventing them from leaving the waveguide, as shown schematically in FIG. 7B. For example, the angles of incidence of the rays striking the surface can be greater than the minimum angle required for causing TIR at the waveguide/air interface (See above Eq. 1) to ensure total internal reflection of those rays.

In contrast, when the waveguide's surface 19B is in optical contact with the skin (FIG. 7A), the rays reflected by the sidewall 19a pass through the surface 19B to enter the skin. (The waveguide/skin interface does not cause total internal reflection of those rays). The use of TIR provides an additional safety mechanism that prevents inadvertent exposure to the radiation coupled to the waveguide (e.g., exposure of a user's eye) by ensuring that radiation is emitted through the waveguide to the external environment only when the waveguide is in contact with the skin. It also increases the sensitivity of the contact sensor, because it utilizes the principle of TIR twice.

The device 16 also includes a detector 10 that is optically coupled to waveguide 19 via a filter 8 and polarizer 7. Detector 10 detects radiation that is diffusely back-reflected (backscattered) from the skin. The device 16 also includes an optical sensor 11 having a detector 11a optically coupled to a filter 9, which can determine whether the waveguide is in contact with the skin, also in a manner similar to the detector 11 as described in conjunction with FIG. 1A. However, as described in conjunction with FIG. 1A, the operation of the device is reversed. In other words, where device 1 as shown in FIG. 1A senses contact when it receives a level of light that exceeds a particular threshold, device 16 senses contact when it receives a level of light that is below a particular threshold. Like the previously described embodiments, detector 11a is optically coupled to waveguide 19 via a filter 9. Unlike the previous embodiments, the detector 11a is also optically coupled to waveguide 19 via a polarizer 4 located between filter 9 and waveguide 19. Polarizer 4 has a polarization axis that is orthogonal to that associated with the source polarizer 3. Thus, device 16 suppresses the detection of specular reflections at both detectors 10 and 11a. Further, the filters 8 and 9 block ambient radiation from reaching the detectors.

Figure 8A:
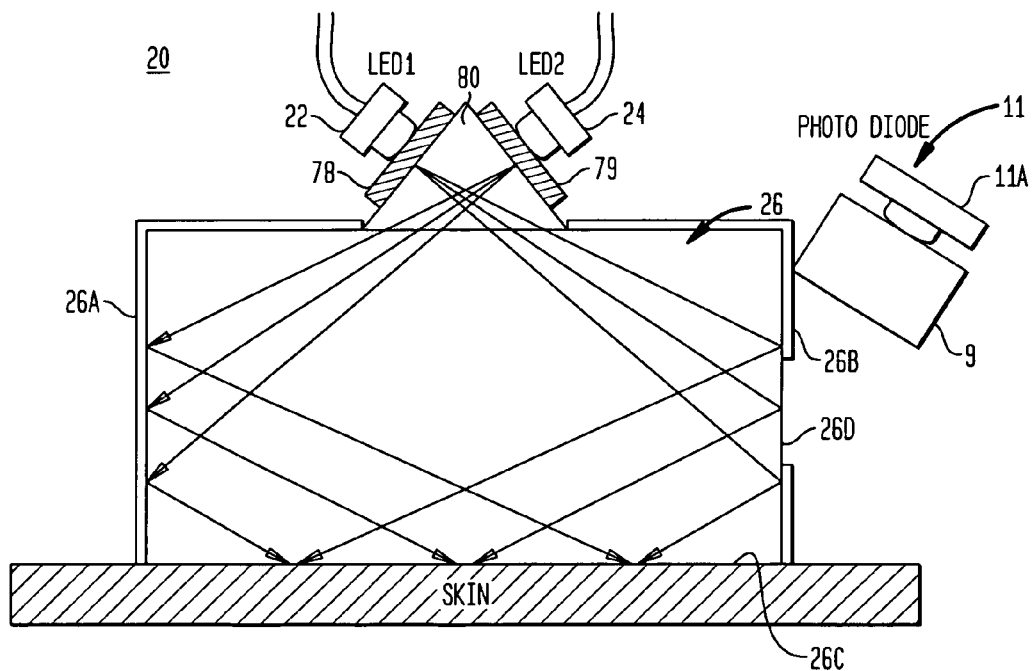
FIG. 8A is a schematic side view of a dermatological device according to another embodiment of the invention that includes two radiation sources capable of generating radiation at different wavelengths and a waveguide having reflective sidewalls for reflecting radiation from those sources to the skin.

FIG. 8A schematically depicts a device 20 in accordance with another embodiment of the invention that also relies on reflection of light from reflective sidewalls of a waveguide to couple light into the skin and to inhibit its coupling when there is no contact between the waveguide and the skin. Rather than utilizing a single radiation source, the device 20 includes two radiation sources 22 and 24, each of which generates radiation at a different wavelength (e.g., in a range of 600 nm to 900 nm). The radiation sources 22 and 24 are optically coupled to a waveguide 26 via a prism 18. The waveguide 26 includes two reflective sidewalls 26a and 26b, each of which directs the light received from one of the radiation sources to a surface 26c of the waveguide such that the radiation is internally reflected by that surface in absence of contact between the waveguide and the skin, and is transmitted through that surface to the skin when there is contact. The reflective sidewalls can be formed, e.g., by depositing a reflective material (e.g., silver) on the surfaces of waveguide 18. The waveguide can be formed of a material that is transmissive to the radiation generated by the sources 22 and 24, and, in the present embodiment, is fused silica. Similar to the previous embodiments, the radiation that is backscattered from the skin can be detected by a detector (not shown) whose output signals are analyzed by a processor (not shown) to determine a skin characteristic. Further, the sensor 11 is optically coupled to an opening 26D in the sidewall 26b, which is created by an absence of reflective coating at the opening. The opening allows light to leak from waveguide 26 and be detected by sensor 11.

Device 20 also includes polarizers 78 and 79 and prism 80. Light sources 22 and 24 are optically coupled to waveguide 26 via the polarizers 78 and 79 and the prism 80. Polarizer 78 has a polarization axes that is orthogonal to that associated with polarizer 79, which, as discussed above, serves to eliminate surface and other reflections not associated with the parameter being measured. Additionally, sensor 11 further includes a detector 11a and a filter 9, located between detector 11a and opening 26D. The filter serves to reduce the amount of ambient radiation that reaches the detector 11a.

Figure 8B:
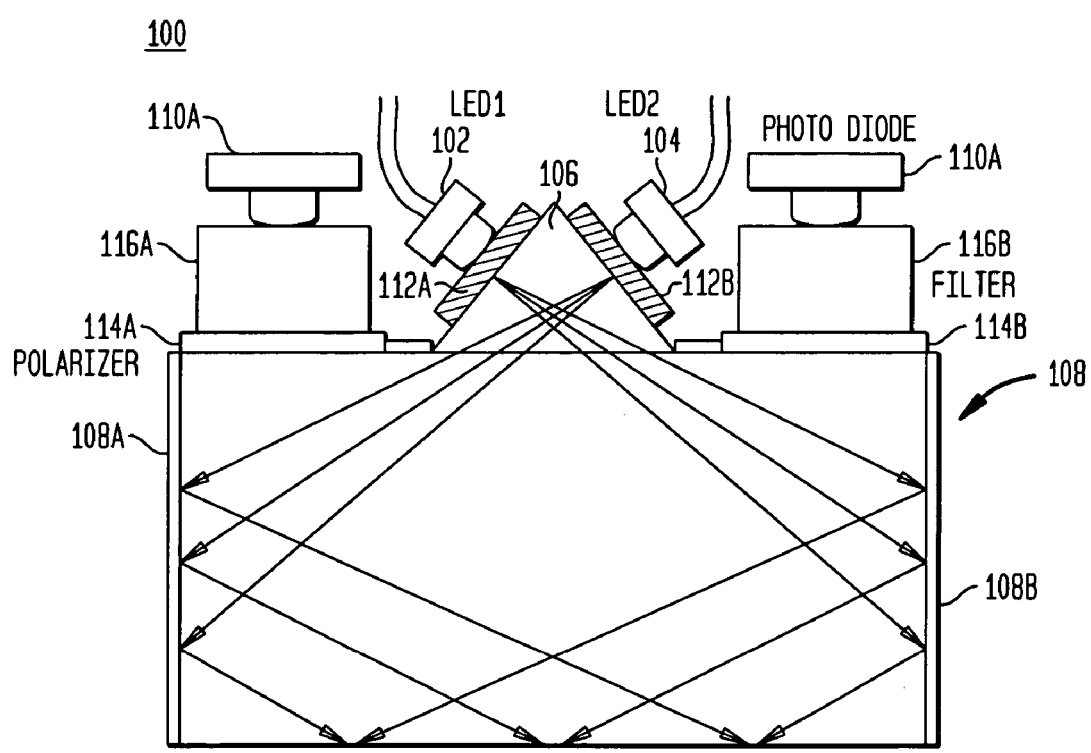
FIG. 8B is a schematic side view of a dermatological device in accordance with another embodiment of the invention that utilizes two radiation source whose radiation is reflected to the skin via reflective sidewalls of a waveguide and further includes two detectors for detecting radiation backscattered from the illuminated skin.

FIG. 8B schematically depicts a device 100 according to another embodiment that utilizes two radiation sources 102 and 104 for illuminating the skin by coupling the radiation via a prism 106 to a waveguide 108 having two reflective sidewalls 108a and 108b, each of which is adapted for directing primarily radiation from one of those sources to the skin. The device 100 further includes two detectors 110a and 110b for detecting radiation backscattered from the skin. As in previous embodiments, the detected backscattered radiation can be analyzed by a processor (not shown) to determine a skin characteristic of interest (e.g., MOD). Similar to some of the previous embodiments, the radiation sources 102 and 104 are coupled to polarizers 112a and 112b, respectively, while the detectors 110a and 110b are coupled, respectively, to orthogonal polarizers 114a and 114b for suppressing the detection of specular reflections. Further, the detectors 110a and 110b are coupled to filters 116a and 116b, which filter out ambient radiation noise.

Figure 9:
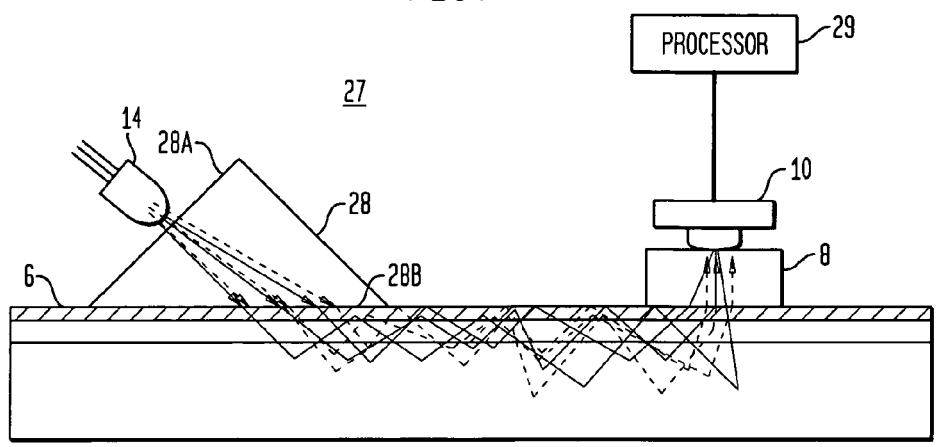
FIG. 9 schematically depicts a dermatological device in accordance with another embodiment of the invention that utilizes a radiation source to couple radiation via a prism to the skin at one location and utilizes a detector optically coupled to the skin at another location to collect at least some of the radiation transmitted through the skin for measuring a characteristic of the skin, such as the melanin optical density.

FIG. 9 schematically depicts a dermatological device 27 according to another embodiment of the invention that relies on the detection of radiation transmitted through tissue 6 (in this case skin) to determine a characteristic of the tissue (in this case MOD). The exemplary device 27 includes a radiation source 14, e.g., one capable of generating radiation of at least two wavelengths in a range of about 600 nm to about 900 nm, that is optically coupled to a prism 28. The prism 28 receives the radiation from the source through a surface 28a thereof and couples that radiation to the skin via another surface 28b, which is adapted for optical contact with the skin. The index of refraction of the material forming the prism can be selected so as to adjust the range of angles at which the radiation traveling through the prism enter the skin via refraction at the prism/skin interface. The process is similar to that described above in conjunction with device 1.

The device 27 further includes a detector 10, which is coupled to a filter 8, which filters out ambient radiation. The detector 10 is positioned at a predetermined distance from the prism to detect at least a portion of the radiation coupled by the prism 28 into the skin and transmitted through a skin portion separating the prism 28 from the detector 10. The precise angle of prism 28 and the distance between prism 28 and detector 10 can be selected to optimize a particular design, and several angles and distances could be used, some being more optimal than others. In the present embodiment, the angle at which radiation is directed to the tissue 6 is approximately 45 degrees, and the distance between prism 28 and detector 10 is approximately 1 cm. In the above device 27, the distance between the source and the detector can be adjusted to tune the device for measuring the concentration of a given chromophore (pigment) of interest at different skin depths, for example, by selecting wavelengths that are better absorbed by deeper tissues or over longer distances, by adjusting the distance between the prism 28 and the detector 10, and/or by utilizing additional wavelengths and/or detectors to differentiate the relative amounts of the chromophore at different positions or depths in the tissue 6.

The light entering the skin is transmitted diffusely (via multiple scattering and/or reflections events) to the detector. The transmitted light can also carry information regarding the concentration of a chromophore of interest, as a result of its interaction with that chromophore (e.g., via absorption of some of the light by the chromophore). A processor 29 in electrical communication with the detector 10 and light source 14 analyzes the detector's output signals generated in response to illumination of the skin at two or more radiation wavelengths (e.g., two wavelengths in a range of about 600 nm to about 900 nm) to determine a characteristic of the skin, such as melanin optical density.

Figure 10:
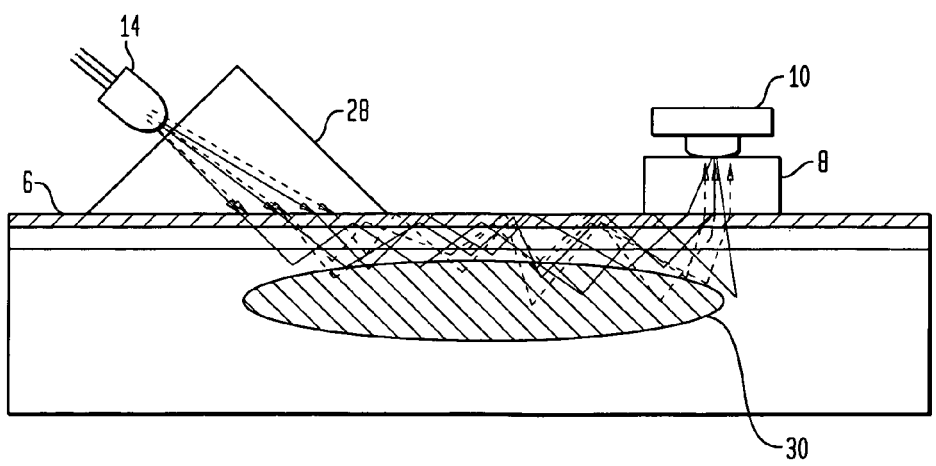
FIG. 10 schematically depicts the use of the device of FIG. 9 placed above and detecting the iris of a human eye.

The device 27 provides a high sensitivity in measuring the concentration of a pigment of interest, as it relies on diffuse transmission of photons over a long distance through the skin. This allows the device to be employed in a variety of applications. By way of example, as shown schematically in FIG. 10, the device 27 can be employed to detect an iris 30 within the eye. For example, as the device 27 is scanned over the skin, it can detect significant absorption of the radiation transmitted through the illuminated skin (especially at wavelengths in a range of about 600 to about 800 nm) by the iris 30, thereby detecting its presence. Such detection of the iris can be useful, for example, in devices that must avoid damaging an eye when providing laser or other radiation treatment to the skin. The device 27 can be incorporated in such treatment devices to provide a signal when the treatment device is over the eye, and preferably inhibit activation of (or deactivate) the treatment laser source based on such eye detection signal.

Figure 11A:
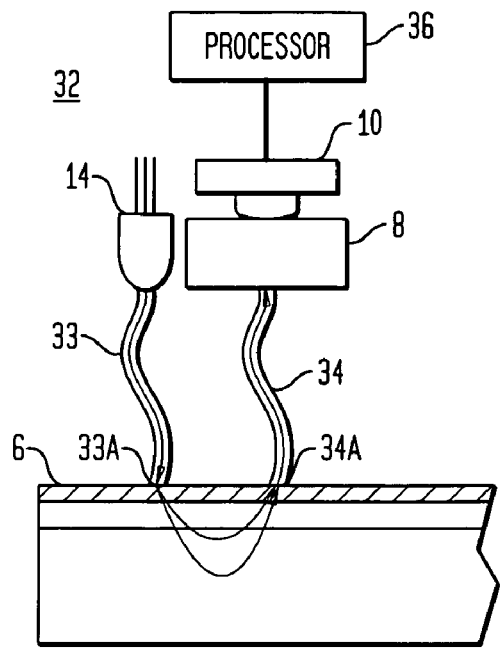
FIG. 11A schematically depicts a dermatological device in accordance with another embodiment of the invention that employs optical fibers for coupling radiation into the skin and for collecting radiation backscattered from the skin.

In other embodiments, the dermatological devices of the invention can employ optical fibers for coupling radiation from a source into the skin and/or decoupling radiation backscattered by or transmitted through an illuminated skin segment. By way of example, FIG. 11A schematically depicts a dermatological device 32 according to such an embodiment of the invention that includes a source 12 optically coupled to a plurality of optical fibers 33, each of which receives the radiation generated by the source at one end thereof and, during operation, can be optically coupled at another end to a tissue 6 (in this case, skin). In many embodiments, the source 12 is capable of generating radiation at two or more wavelengths, e.g., two or more wavelengths in a range of about 600 nm to about 900 nm. The device 32 further includes another set of optical fibers 34, each of which is optically coupled at one end thereof to the skin at a location separated by a selected distance from the location at which the radiation enters the skin via the fibers 33a. In this manner, the optical fibers 34 collect at least a portion of the radiation that is diffusely transmitted (radiation transmitted via multiple scattering and/or reflection events) through a skin portion disposed between the ends 33a of the fibers 33 and the ends 34a of the fibers 34, and is coupled into the fiber 34, e.g., via scattering/reflection events. Each of the optical fibers 34 is optically coupled at another end, via the a filter 8 that filters out ambient radiation noise, to a detector 10 that receives the radiation collected by the optical fibers 34.

A processor 36 processes the output signals of the detector 10 to determine a characteristic of the illuminated skin segment. For example, in cases where a measurement of the melanin optical density of the skin is desired, the source 14 can be selected to provide at least two radiation wavelengths in a range of about 600 nm to about 900 nm. The source can be activated to illuminate the skin 6 via the fibers 33 at these two wavelengths in different temporal intervals. And the output detection signals generated by the detector 10 corresponding to the two illumination wavelengths can be analyzed by the processor 36 to determine the melanin concentration by utilizing, e.g., the mathematical equations discussed above.

Figure 11B:
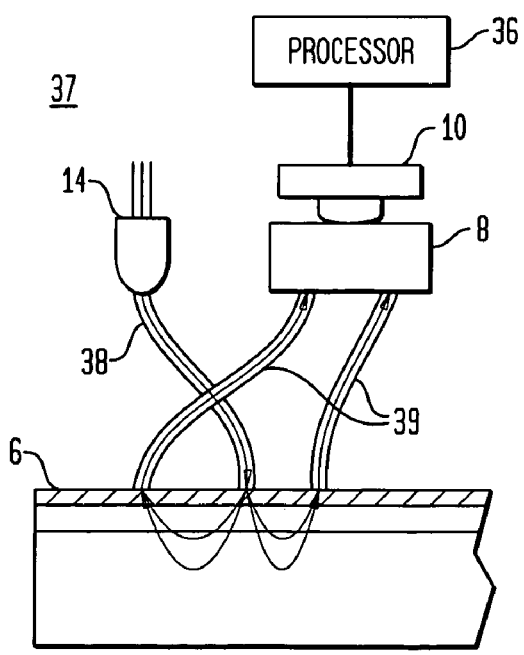
FIG. 11B schematically depicts another embodiment of a dermatological device according to the teachings of the invention that employs one or more optical fibers for coupling radiation into the skin and an annular waveguide for collecting radiation that is backscattered from the skin.
Figure 11C:
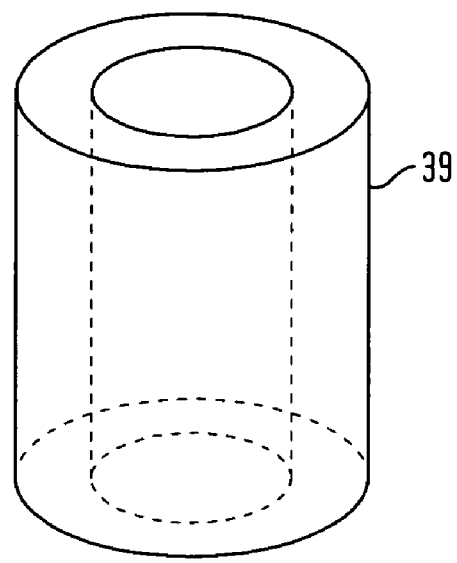
FIG. 11C is a perspective schematic view of an exemplary annular waveguide suitable for use in the device of FIG. 11B.

In another embodiment schematically shown in FIG. 11B, a dermatological device 37 in accord with the teachings of the invention includes a plurality of optical fibers 38 for transmitting the radiation generated by a source 14 to tissue 6. Waveguides 39 guide the radiation from tissue 6 to a detector 10. Waveguides 39 have a substantially cylindrical hollow structure, as shown in FIG. 11C. Waveguides 39 collect at least a portion of the radiation transmitted through the skin from the illumination site to the waveguide. A detector 10 is optically coupled to the waveguide, via a filter 8, to receive the radiation collected by the waveguide. Similar to the previous embodiment, a processor 36 operates on the output signals generated by detector to determine a desired characteristic of the skin.

Figure 11D:
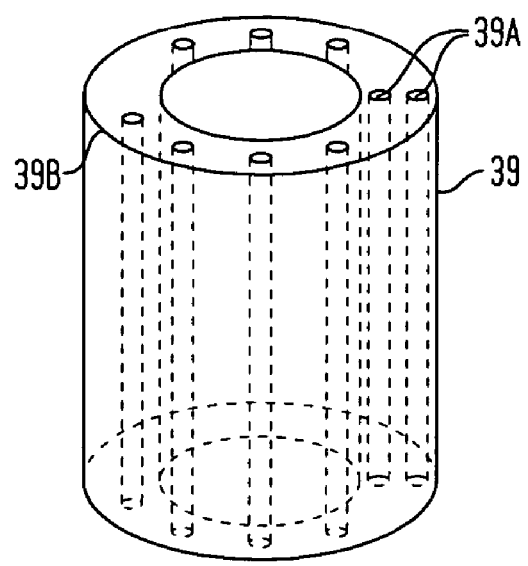
FIG. 11D is a perspective schematic view of an annular waveguide suitable for use in the device of FIG. 11B, which comprises a plurality of optical fibers disposed in an annular enclosure.
Figure 11E:
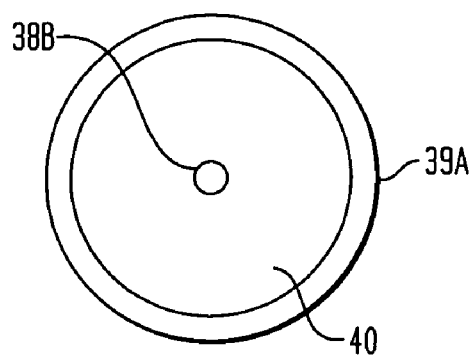
FIG. 11E is a schematic top view of a surface area of the skin illuminated by a radiation source of the device of FIG. 11B as well as an area coupled to the annular waveguide of that device through which backscattered radiation is collected.

As shown in FIG. 11D, in some embodiments, the cylindrical waveguide is formed by disposing a plurality of optical fibers 39a within an annular housing 39b, e.g., a flexible enclosure. In some alternative embodiments, the waveguide can be an annulus formed of a suitable material, such as fused silica. By way of further illustration, FIG. 11E schematically depicts a top view of an area 40 under observation (the sensing area) by the device 37. The perimeter of the sensing area is defined by a proximal end of the cylindrical waveguide 39 shown in FIGS. 11C and 11D. The radiation energy is coupled into the area 40 via a proximal end of optical fibers 38 (the area 38b illustrates the top view of the skin area illuminated by the fibers 38). In this embodiment, the waveguide can be selected such that sensing area is large so as to reduce measurement sensitivity to local irregularities. However, other embodiments can be sized to provide relatively larger sensing areas or relatively smaller sensing areas. Additionally, alternate embodiments can include other configurations such as an internal waveguide located inside waveguide 39 that replaces fibers 38. Similarly, light can be provided to the sensing area through a hollow space within the waveguide 39 without using fibers 38 or another waveguide.

Figure 12:
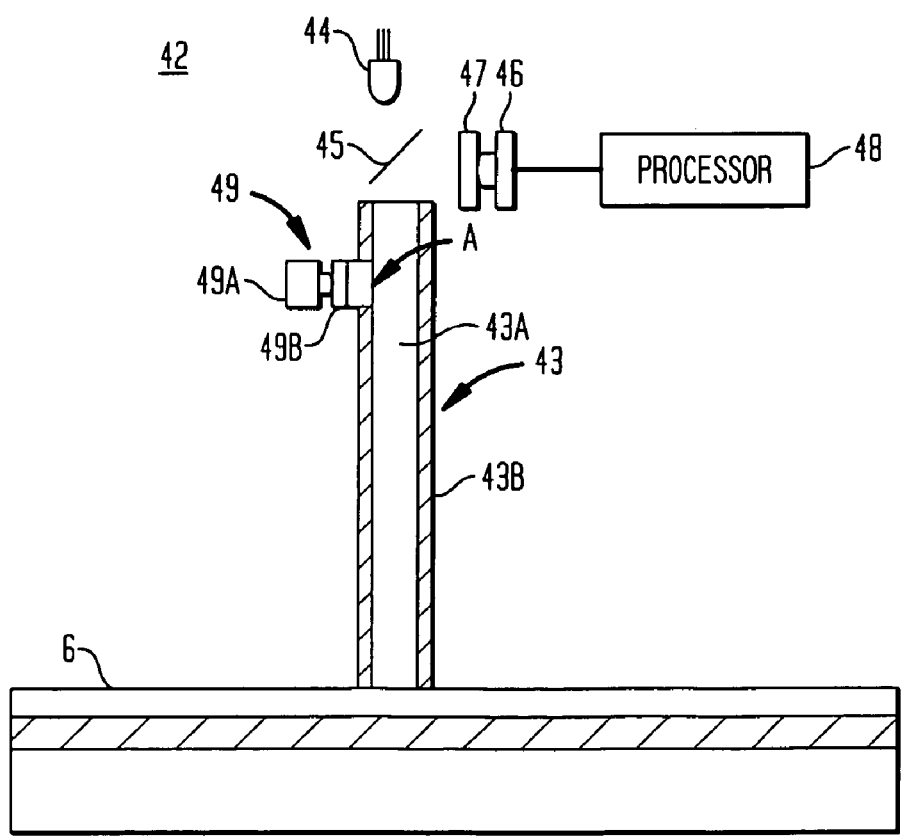
FIG. 12 is a schematic side view of a device in accordance with another embodiment of the invention that employs an optical fiber for transmitting radiation received from a source at a proximal end thereof to the skin via its distal end.

By way of another example, FIG. 12 schematically depicts a dermatological device 42 that includes an optical fiber 43. Optical fiber 43 comprises a core 43a surrounded by a cladding 43b. Optical fiber 43 is optically coupled at a proximal end thereof to a radiation source 44 to receive radiation from the source after its passage through a beam splitter 45, and is coupled at its distal end to a skin region 6 to transmit the received radiation to the skin. The radiation that is backscattered into the fiber from the illuminated skin region travels back through the fiber along the same path and exits from the proximal end towards the beam splitter 45, which in turn directs the backscattered radiation to a detector 46, which is coupled to a filter 47. A processor 48 determines one or more characteristics of the skin based on the output signals generated by the detector. By way of example, in some embodiments, the radiation source 44 provides two or more radiation wavelengths, e.g., two or more wavelengths in a range of about 600 nm to about 900 nm, and the processor analyzes the output signals of the detector 46 corresponding to backscattered radiation at these wavelengths to determine a skin characteristic (e.g., melanin concentration), e.g., in a manner discussed above.

In this embodiment, the device 42 further includes an optical sensor 49, having a detector 49*a* coupled to a filter 49*b*, that is optically coupled to the fiber 43 at a fiber section A from which the cladding is removed. The removal of the cladding allows a portion of the backscattered radiation to leak from the core into the sensor's detector. The detection signal generated by the sensor's detector can then be utilized to determine whether the fiber's distal end is in contact with the skin. For example, the detection of radiation intensity below a selected threshold by the sensor can indicate lack of contact between the fiber's distal end and the skin while the detection of radiation above that threshold can indicate contact.

Figure 13:
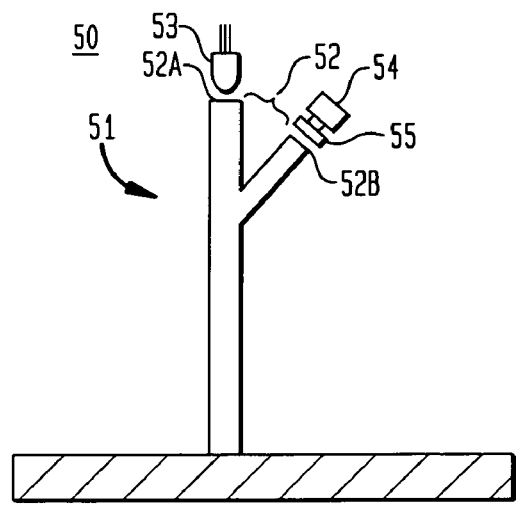
FIG. 13 schematically depicts another embodiment of a dermatological device according to the teachings of the invention that includes an optical fiber having a split end to provide an input port for receiving radiation from a source and output port for coupling backscattered radiation collected at its distal end to a detectors.

FIG. 13 schematically depicts a dermatological device 50 in accordance with another embodiment of the invention that also employs an optical fiber 51 for coupling radiation into the skin and collecting radiation backscattered from the illuminated skin. More specifically, optical fiber 51 has a split end 52 that provides an input port 52*a* optically coupled to a radiation source 53 for receiving radiation from the source, and an output port 52*b* for coupling radiation backscattered into the fiber to a detector 54, via a filter 55. Similar to some of the previous embodiments, the source can provide two or more wavelengths of interest and the output of the detector 54 corresponding to the backscattered radiation at those wavelengths can be analyzed by a processor (not shown) to determine a skin characteristic (e.g., the skin's melanin index).

Although the majority of the embodiments described herein are used for the measurement of MOD of skin by applying radiation at the surface of the skin, other embodiments are possible, both for measuring other characteristics and other tissues. For example, given the potentially small size of the embodiments described in conjunction with FIGS. 11A-13, alternate embodiments of devices employing these concepts could be use to measure physical properties of internal tissues, for example, via an endoscope and/or incision.

A diagnostic dermatological device according to the teachings of the invention, such as those discussed above, can be coupled to a dermatological treatment device to provide information regarding one or more characteristics of the skin to be treated. For example, as shown schematically in FIG. 14, a dermatological device 56 can include a treatment module 57 and a diagnostic module 58 that is in communication with the treatment module. By way of example, the treatment module can include a radiation source 59 that provides treatment radiation. The treatment radiation can be coupled via one or more optics (not shown) through a radiation transmissive window 60 (such as a sapphire window) to the skin. Alternatively, the treatment module can receive the treatment radiation from an external source, e.g., via an optical fiber. By way of example, U.S. patent application Ser. No. 10/154,756 entitled "*Cooling System for a Photocosmetic Device*," which is herein incorporated by reference, provides teachings regarding dermatological treatment devices that can be employed in constructing the treatment module 57. In this embodiment, the treatment module includes a feedback mechanism 62 that is in communication with the treatment source 59 and the diagnostic module 58. The feedback mechanism 62 can receive signals from the diagnostic module indicative of one or more skin characteristics, e.g., the melanin optical density.

In this exemplary embodiment, the feedback mechanism 62 applies control signals to the radiation source in response to the information regarding the skin characteristic received from the diagnostic module to adjust one or more parameters of the treatment radiation generated by the source, e.g., the power of treatment radiation, the wavelength of the treatment radiation, pulse width and/or pulse repetition rate when pulsed radiation is used, or any other parameter of interest. In some cases, the diagnostic module can be utilized to allow activation of the treatment source only for treating certain skin types. For example, the treatment radiation source can be activated to treat only those persons whose skin pigment levels (e.g., MOD) would result in the diagnostic wavelength signal, the ratio of the diagnostic signals at different wavelengths, as well as the background signals falling within predefined ranges (e.g., above or below certain thresholds.) By way of example, such parameters can be set such that most materials other the skin would provide diagnostic signals outside a range that would be acceptable for activating the treatment source. For example, when the skin characteristic corresponds to the MOD, the feedback module can control the treatment source to adjust its output power, e.g., to reduce the power when the measured melanin optical density is high and to increase it when that optical density is low. Further, in some cases in which the skin melanin concentration is above a predefined threshold, the feedback mechanism can inhibit activation of the treatment source. This can be utilized, e.g., as a safety measure to ensure that the treatment radiation is applied only when appropriate (e.g., only to the skin having pigment levels within a predefined range).

In some embodiments, such adjustment of one or more parameters of the treatment radiation in response to the information provided by the diagnostic module can be accomplished in real-time. For example, as the device 56 is moved over the skin, the treatment module 57 lags behind the diagnostic module 58 such that the diagnostic module determines a desired characteristic of a skin segment to be treated prior to application of the treatment radiation to that segment by the treatment module. In this manner, the treatment module can utilize the information provided by the diagnostic module to adjust the treatment parameters (e.g., the power level of the treatment radiation) in real-time. For example, different portions of a skin patch under treatment can exhibit different pigment levels (e.g., different melanin concentrations). In such a case, the treatment module can adjust the power level of the treatment radiation as the treatment radiation is applied to those skin portions.

In embodiments in which the treatment source is external to the treatment module, the adjustment of one or more parameters of the treatment radiation in response to information provided by the diagnostic module can be achieved, e.g., by applying control signals to the source and/or to one or more elements disposed in the treatment module and in optical coupling with the source. For example, a shutter disposed within the treatment module can be controlled to allow or inhibit application of the treatment radiation to the skin based on one or more skin characteristics determined by the diagnostic module. Further, one or more neutral density filters can be utilized to modulate the power level of the treatment radiation.

Figure 14:
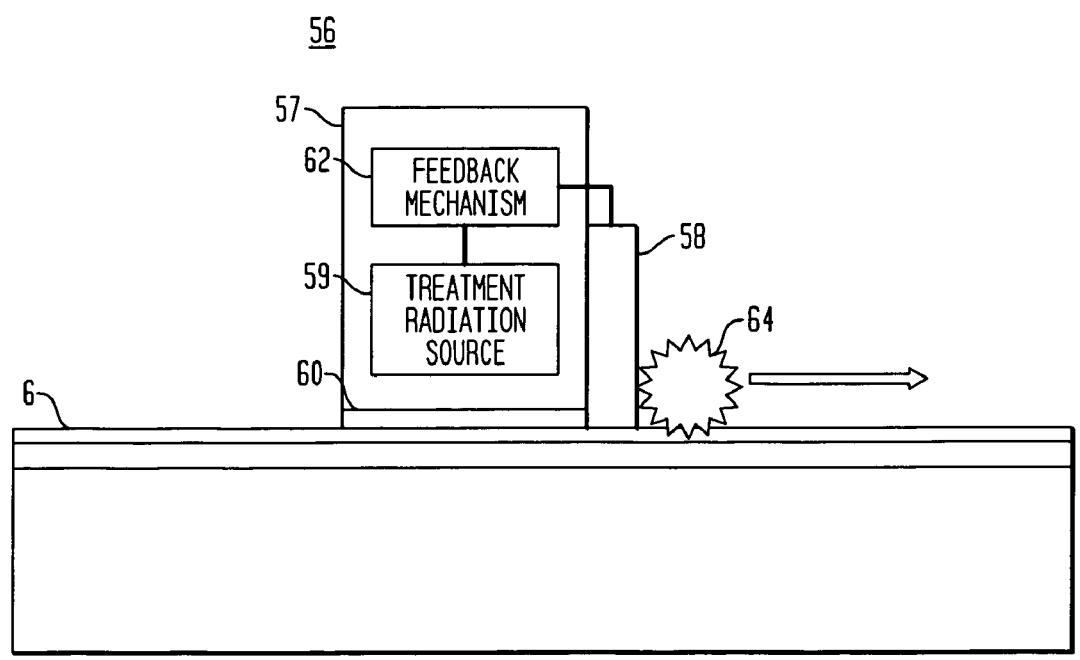
FIG. 14 schematically depicts a dermatological device according to an embodiment of the invention having a treatment module and a diagnostic module, which is constructed in accordance with the teachings of the invention.

With continued reference to FIG. 14, the exemplary device 56 further includes a speed sensor 64 the measures the device's scanning speed as it scans the skin. The speed sensor can be configured to allow a directional scan (uni-directional in this case, although other embodiments are possible, including bi-directional and multi-directional) such that the diagnostic module 58 would lead the treatment module. Examples of speed sensors suitable for use in the device 56 can be found in U.S. patent application Ser. No. 11/098,015, filed Apr. 1, 2005 entitled "*Methods and products for producing lattices of EMR-treated islets in tissues, and uses therefore*," which is herein incorporated by reference. In some embodiments, the feedback mechanism can be incorporated within the speed sensor.

In some embodiments, the treatment and the diagnostic modules, and in some cases the speed sensor as well, can be integrated within a single enclosure so as to provide a compact device. Further, in many such embodiments, the diagnostic and the treatment sources can share a common optical path so that a tissue region can be treated in real-time as its one or more characteristics (such as melanin optical density) are measured. Such a device can be particularly useful when the treatment is applied in a stamping mode.

Figure 15:
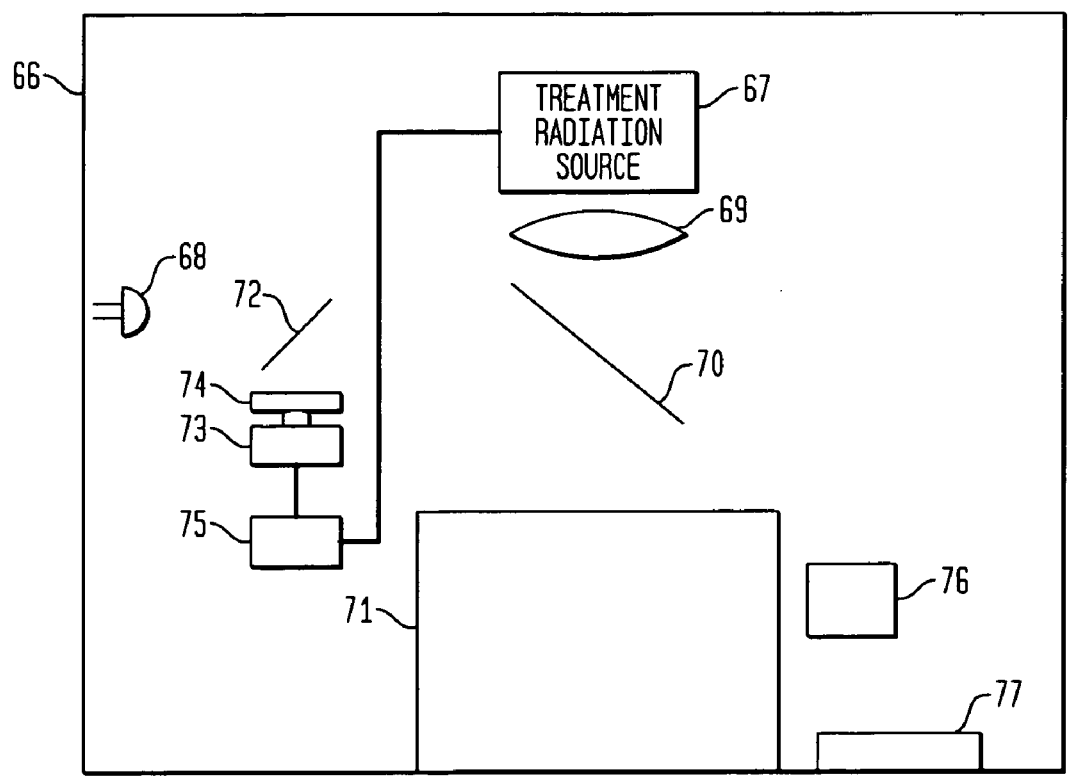
FIG. 15 schematically depicts a dermatological device according to an embodiment of the invention designed to provide both diagnostic and treatment capabilities in a compact enclosure.

By way of example, FIG. 15 schematically depicts a dermatological device 65 having an enclosure 66 in which a treatment radiation source 67 for generating treatment radiation and a radiation source 68, e.g., a source generating two or more wavelengths are disposed. The radiation from the treatment source is coupled via a lens 69, after passage through a beam splitter 70, into a waveguide 71, e.g., a sapphire block. The radiation from the source 68 passes through a beam splitter 72 to be reflected by the beam splitter 70 into the waveguide. The waveguide 71 guides both the treatment and the radiation into a skin region in contact therewith. A portion of the radiation that is backscattered from the illuminated skin region is reflected by the beam splitters 72 and 70 into a detector 73 via a filter 74. Detector 73 generates output signals that can be analyzed by a processor 75, e.g., in a manner discussed in connection with the previous embodiments, to determine a characteristic of the tissue 6 (e.g., the melanin concentration of skin). The device 65 can further include an optical sensor 76, such as those discussed above, that is optically coupled to a sidewall of the waveguide 71 for determining contact between the waveguide and the skin. The processor can operate on the output signals generated by the sensor to control the treatment radiation source (e.g., inhibit its activation and/or deactivate it when there is no contact between the waveguide and the skin). In addition, the processor can further adjust one or more parameters of the treatment radiation (e.g., power level, pulse width, or repetition rate) in response to the output signals of the optical sensor 76. Similar to certain embodiments discussed above, a plurality of polarizers and filters can be employed to suppress detection of radiation specularly reflected at various interfaces and/or ambient radiation. Further, in some embodiments, the device 65 can include a speed sensor 77 that can measure the speed of the device 65 as it is scanned over the skin, and in some cases apply control signals to the treatment source (e.g., modulate the source's power in response to the scan speed).

In other embodiments, more than two wavelengths can be used to detect a physical property of the skin. For example, by using three wavelengths, the apparent age of the skin can be determined. The backscattered radiation from a skin region can be measured using three or more wavelengths. Although many wavelengths are possible, the wavelengths chosen are preferably in a range of about 600 nm to about 900 nm, such as 645, 700 and 900 nm. As in the case of measuring MOD, selection of wavelengths in this range takes advantage of the absorption characteristics of skin in that wavelength range. The age of the skin can correspond to its chronological age or its apparent age. For example, in some cases, the skin of a young individual (e.g., a person in her twenties) may nonetheless exhibit a much older apparent age, e.g., due to excessive sun exposure and/or smoking. The devices discussed above can be employed to practice this aspect of the invention, e.g., by selecting an appropriate radiation source (or sources) that provide the requisite radiation wavelengths. Reflectance values at these three wavelengths can be analyzed to determine MOD and skin diffusion properties, and the skin age can be correlated to the skin diffusion properties.

Similarly, by using three or more wavelengths, the error in measurement can be reduced. For example, two wavelengths can be selected that are close in value (e.g., approximately 10 nm apart) while the third wavelength is further spaced, e.g., 640, 650 and 700 nm. The use of the additional wavelength will help reduce errors due to inconsistencies in measurements caused by other physical characteristics of the tissue.

In some embodiments, the wavelength of the radiation generated by a radiation source utilized for providing radiation can depend to some degree on the temperature of that source. In such embodiments, wavelength versus temperature data for the radiation source(s) can be stored, e.g., on a memory module, to be utilized by the processor to calibrate the radiation wavelength (to calculate the actual wavelength from the nominal wavelength).

Although the above embodiments generally described utilizing wavelengths in a range of about 600 nm to about 900 to measure, e.g., the MOD of skin, the various embodiments discussed above can be generally employed with radiation source generating radiation with wavelengths in other ranges including a range of about 300 nm to about 1200 nm to measure the concentration of other chromophores (such as hemoglobin). For example, two forms of hemoglobin have primary absorption bands in a spectral range of 405 nm to 430 nm (the Soret band) and secondary bands in a range of 540 nm to 580 nm. In some embodiments, the concentration of the hemoglobin can be measured by detecting the backscattered radiation at two or more wavelengths in those bands. Even broader or different wavelength ranges can be used for other purposes or to use other types of radiation sources.

Those having ordinary skill in the art will appreciate that various modifications can be made to the above embodiments without departing from the scope of the invention.

What is claimed is:

1. A dermatological treatment device, comprising:
a radiation source assembly configured to generate radiation having at least a first wavelength for tissue irradiation;
a waveguide coupled to said source assembly for directing the radiation from the radiation source assembly to a portion of tissue, and having a surface configured to irradiate said portion with said radiation;
a detector optically coupled to a sidewall of said waveguide and configured to detect radiation backscattered from said tissue in response to irradiation from said radiation source assembly and transmitted through the sidewall to the detector, said detector generating signals indicative of the level of radiation detected;
said sidewall being configured such that the level of backscattered radiation reaching the detector changes due to a change in the level of internal reflection of said backscattered radiation incident on said sidewall based on absence or presence of contact between said surface of the waveguide and the tissue; and a processor configured to process the level of radiation detected and indicating at least one of contact of said surface of the waveguide with said tissue, absence of contact of said surface of the waveguide with said tissue, and one or more characteristics of said tissue.

2. The device of claim 1, wherein said radiation source assembly includes two or more radiation sources.

3. The device of claim 2, wherein a first radiation source is configured to produce radiation having said first wavelength and wherein a second radiation source is configured to produce radiation having a second wavelength.

4. The device of claim 1, wherein said radiation source assembly includes a single radiation source.

5. The device of claim 4, wherein said radiation source is configured to produce radiation having said first wavelength and radiation having a second wavelength.

6. The device of claim 1, wherein said radiation source assembly includes at least one of a light emitting diode (LED), a bi-color LED, a tunable radiation source, and a laser radiation source.

7. The device of claim 1, wherein said radiation source assembly is configured to generate radiation having a second wavelength.

8. The device of claim 7 wherein said first and second wavelengths are selected from a range of about 350 nm to about 1200 nm.

9. The device of claim 7 wherein said first and second wavelengths are selected from a range of about 600 nm to about 900 nm.

10. The device of claim 1 wherein said first wavelength is selected from a range of about 350 nm to about 1200 nm.

11. The device of claim 1 wherein said first wavelength is selected from a range of about 600 nm to about 900 nm.

12. The device of claim 1, wherein said detector is configured to detect a level of said radiation of said first wavelength.

13. The device of claim 1, wherein said detector is configured to send a signal to said processor indicating that said surface of said waveguide is not in contact with said tissue when the level of radiation detected is below a threshold.

14. The device of claim 1, wherein said detector is configured to send a signal to said processor indicating that said surface of said waveguide is in contact with said tissue when the level of radiation detected is above a threshold.

15. The device of claim 1, wherein said detector is configured to send a signal to said processor indicating that said surface of said waveguide is not in contact with said tissue when the level of radiation detected is above a threshold.

16. The device of claim 1, wherein said detector is configured to send a signal to said processor indicating that said surface of said waveguide is in contact with said tissue when the level of radiation detected is below a threshold.

17. The device of claim 1, wherein said waveguide is configured to totally internally reflect said backscattered radiation along the sidewall when said surface of said waveguide is not in contact with said tissue.

18. The device of claim 1, wherein said waveguide is configured to not totally internally reflect said backscattered radiation along the sidewall when said surface of said waveguide is in contact with said tissue.

19. The device of claim 1 wherein said waveguide is configured to totally internally reflect said backscattered radiation along the sidewall when said surface of said waveguide is in contact with said tissue.

20. The device of claim 1, wherein said waveguide is configured to not totally internally reflect said radiation along the sidewall when said surface of said waveguide is not in contact with said tissue.

21. The device of claim 1, wherein said radiation source assembly is configured to generate radiation having a second wavelength, and said detector is configured to detect a level of said radiation of said first wavelength and of said second wavelength.

22. The device of claim 1, further comprising:
a first polarizer configured to filter radiation of a first polarity from said radiation source assembly; and
a second polarizer configured to filter radiation of a second polarity entering said detector.

23. The device of claim 1, further comprising a filter disposed between the detector and the waveguide.

24. The device of claim 1, wherein said radiation source assembly is configured to generate radiation having three or more wavelengths.

25. The device of claim 24, wherein said radiation source assembly generates a wavelength selected from the group of about 645 nm, about 700 nm, and about 900 nm.

26. The device of claim 1 wherein said waveguide is formed of a material having an index of refraction in a range of about 1.4 to about 2.5.

27. The device of claim 1, further comprising:
a first polarizer configured to filter radiation of a first polarity from said radiation source assembly; and
a second polarizer configured to filter radiation of a second polarity entering said detector.

28. The device of claim 1, further comprising a filter disposed between said waveguide and said detector.

29. The device of claim 1, further comprising a controller coupled to said radiation source assembly, said controller configured to activate said radiation source assembly to produce radiation of different wavelengths at different times.

30. The device of claim 1, wherein said waveguide is an optical fiber.

31. The device of claim 1, further comprising at least one additional waveguide coupled to said source assembly.

32. The device of claim 31, wherein said at least one additional waveguide is an optical fiber.

33. The device of claim 1, wherein the one or more characteristics of the tissue comprises melanin optical density (MOD).

34. The device of claim 33, wherein said radiation source assembly generates a wavelength selected from the group of about 645 nm, about 700, and about 900 nm.

35. A dermatological device for determining a physical characteristic of a portion of skin, comprising
a radiation source assembly configured to generate radiation having at least a first wavelength;
a waveguide coupled to said source assembly for directing the radiation from the radiation source assembly to said portion of skin, and having a surface configured to irradiate said portion with said radiation;
a first detector coupled to said waveguide and configured to detect radiation backscattered from said portion of skin in response to irradiation from said radiation source assembly, said detector generating signals indicative of the level of radiation detected;
a second detector optically coupled to a sidewall of said waveguide for indicating contact of said surface of the waveguide with said portion of skin or absence of contact of said surface of the waveguide with said portion of skin;
said sidewall being configured such that the level of backscattered radiation reaching the second detector changes due to a change in the level of internal reflection of said backscattered radiation incident on said sidewall based on absence or presence of contact between said surface of the waveguide and the tissue; and a processor in communication with said first detector and said second detector configured to process said signals from the first detector to determine the melanin optical density of said portion of skin, and configured to process signals from the second detector to determine contact or absence of contact of said surface of the waveguide with said portion of skin.

36. The device of claim 35, wherein said first wavelength is approximately 645 nm.

37. The device of claim 35, wherein said first wavelength is approximately 700 nm.

38. The device of claim 35, wherein said surface of said waveguide is adapted for contact with the tissue and inhibits transmission of radiation in absence of skin contact by total internal reflection of radiation reflected thereto from a sidewall of said waveguide.

39. The device of claim 35, further comprising a feedback mechanism in communication with said second detector and said radiation source assembly, wherein said feedback mechanism is capable of inhibiting activation of the radiation source assembly when the second detector indicates lack of contact between the waveguide and the source.

40. The device of claim 35, wherein said waveguide is an optical fiber.

41. The device of claim 35, further comprising at least one additional waveguide.

42. The device of claim 35, wherein a first radiation source produces radiation having the first wavelength and wherein a second radiation source produces radiation having a second wavelength.

43. The device of claim 42, wherein said first and second wavelengths are in a range of about 300 nm to about 1200 nm.

44. The device of claim 42, wherein said first and second wavelengths are in a range of about 600 nm to about 900 nm.

45. The device of claim 42, wherein said first and second wavelengths are in a range of about 630 nm to about 730 nm.

46. The device of claim 42, wherein said first wavelength is approximately 645 nm and said second wavelength is approximately 700 nm.

47. The device of claim 35, wherein said radiation source assembly generates a wavelength selected from the group of about 645 nm, about 700 nm, and about 900 nm.

* * * * *